(12) United States Patent
Soliz et al.

(10) Patent No.: US 10,732,098 B1
(45) Date of Patent: Aug. 4, 2020

(54) SELF-INDICATING COLORIMETRIC RESPONSE MATERIALS FOR REMOVAL AND SENSING OF TOXIC CHEMICALS AND NARCOTICS

(71) Applicant: U.S. Army Edgewood Chemical Biological Center, APG, MD (US)

(72) Inventors: Jennifer R Soliz, Ellicott City, MD (US); Darren K Emge, Glen Burnie, MD (US); Ian J. Pardoe, Edgewood, MD (US); Gregory W Peterson, Belchamp, MD (US)

(73) Assignee: The United States of America as Represented by the Secretary of the Army, Washington, DC (US)

(*) Notice: Subject to any disclaimer, the term of this patent is extended or adjusted under 35 U.S.C. 154(b) by 298 days.

(21) Appl. No.: 15/964,850

(22) Filed: Apr. 27, 2018

Related U.S. Application Data

(63) Continuation-in-part of application No. 14/743,425, filed on Jun. 18, 2015, now Pat. No. 9,958,397.
(Continued)

(51) Int. Cl.
*G01N 21/78* (2006.01)
*G01N 21/29* (2006.01)
(Continued)

(52) U.S. Cl.
CPC ........ *G01N 21/251* (2013.01); *B01J 20/0285* (2013.01); *B01J 20/0288* (2013.01);
(Continued)

(58) Field of Classification Search
CPC .......... G01N 33/0037; G01N 33/0042; G01N 33/0044; G01N 33/0047; G01N 33/0049; G01N 33/0052; G01N 33/0054; G01N 33/0057; G01N 33/20; G01N 33/203; G01N 33/227; G01N 33/94; G01N 21/25; G01N 21/29; G01N 21/77; G01N 21/78; G01N 21/783; G01N 21/251; G01N 2021/775; G01N 2021/755; Y10T 436/15; Y10T 436/175383; Y10T 436/178459; Y10T 436/18; Y10T 436/182; Y10T 436/184;
(Continued)

(56) References Cited

U.S. PATENT DOCUMENTS 8,530,719 B1 * 9/2013 Peterson .................. A62D 3/36 588/315
9,770,703 B1 * 9/2017 Soliz .................. B01J 20/28009
(Continued)

*Primary Examiner* — Maureen Wallenhorst
(74) *Attorney, Agent, or Firm* — Ulysses John Biffoni

(57) ABSTRACT

Processes, compositions, and sensors for sensing a variety of toxic chemicals based on colorimetric changes. Exemplary process for sensing a toxic chemical includes contacting a toxic chemical, or byproduct thereof, with a sorbent that includes a porous metal hydroxide or a porous mixed-metal oxide/hydroxide and a transition metal reactant suitable to react with a toxic chemical or byproduct thereof. The sorbent is contacted with the toxic chemical or byproduct thereof for a sampling time. A difference between a post-exposure colorimetric state of the sorbent and a pre-exposure colorimetric state of the sorbent is determined to thereby detect exposure to, or the presence of, the toxic chemical or byproduct thereof.

7 Claims, 11 Drawing Sheets

Related U.S. Application Data

(60) Provisional application No. 62/020,685, filed on Jul. 3, 2014.

(51) Int. Cl.
| | |
|---|---|
| *G01N 33/94* | (2006.01) |
| *G01N 33/20* | (2019.01) |
| *G01N 21/25* | (2006.01) |
| *G01N 33/22* | (2006.01) |
| *B01J 20/08* | (2006.01) |
| *B01J 20/02* | (2006.01) |
| *B01J 20/26* | (2006.01) |
| *B01J 20/28* | (2006.01) |
| *B01J 20/22* | (2006.01) |
| *G01N 21/75* | (2006.01) |
| *G01N 21/77* | (2006.01) |
| *G01N 33/00* | (2006.01) |

(52) U.S. Cl.
CPC .......... *B01J 20/0296* (2013.01); *B01J 20/08* (2013.01); *B01J 20/223* (2013.01); *B01J 20/26* (2013.01); *B01J 20/28014* (2013.01); *G01N 21/78* (2013.01); *G01N 33/227* (2013.01); *G01N 33/94* (2013.01); *B01J 20/0207* (2013.01); *B01J 20/0218* (2013.01); *B01J 20/0222* (2013.01); *B01J 20/0229* (2013.01); *B01J 20/0237* (2013.01); *B01J 2220/42* (2013.01); *G01N 33/0037* (2013.01); *G01N 33/0042* (2013.01); *G01N 33/0044* (2013.01); *G01N 33/0049* (2013.01); *G01N 33/0052* (2013.01); *G01N 33/0054* (2013.01); *G01N 33/0057* (2013.01); *G01N 2021/755* (2013.01); *G01N 2021/775* (2013.01)

(58) Field of Classification Search
CPC ............... Y10T 436/186; Y10T 436/19; Y10T 436/193333; Y10T 436/25375; Y10T 436/255; B01J 20/0288; B01J 20/28014; B01J 20/08; B01J 20/223; B01J 20/0296; B01J 20/26; B01J 20/0285; B01J 20/0207; B01J 20/0218; B01J 20/0222; B01J 20/0229; B01J 20/0237; B01J 2220/42
USPC ..... 436/73, 79, 80, 81, 83, 84, 85, 100, 113, 436/116, 117, 119, 121, 122, 124, 125, 436/164, 165, 167, 177, 178; 422/400, 422/69, 82.05, 82.09, 86, 88, 527, 534, 422/535

See application file for complete search history.

(56) References Cited

U.S. PATENT DOCUMENTS

| | | | |
|---|---|---|---|
| 9,958,397 B1* | 5/2018 | Peterson | G01N 33/0042 |
| 10,495,592 B1* | 12/2019 | Peterson | G01N 27/026 |
| 2010/0166604 A1* | 7/2010 | Lim | G01N 31/22 |
| | | | 422/400 |
| 2013/0010288 A1* | 1/2013 | Dwyer | A62B 18/088 |
| | | | 356/213 |

* cited by examiner

US 10,732,098 B1

SELF-INDICATING COLORIMETRIC RESPONSE MATERIALS FOR REMOVAL AND SENSING OF TOXIC CHEMICALS AND NARCOTICS

CROSS REFERENCE TO RELATED APPLICATIONS

This application is a Continuation-In-Part application of U.S. patent application Ser. No. 14/743,425 filed on Jun. 18, 2015, now U.S. Pat. No. 9,958,397, which claimed the benefit of priority of provisional patent application Ser. No. 62/020,685 filed on Jul. 3, 2014.

GOVERNMENT INTEREST

The invention described herein may be manufactured, used, and licensed by or for the United States Government.

FIELD OF THE INVENTION

The invention relates to compositions, methods, and devices that may be used to monitor the presence or absence of a hazardous chemical in the environment. More specifically, porous sorbents, specifically metal oxides and metal hydroxides, are provided for the removal of toxic chemicals and the self-indicating color/spectral changes associated with said toxic chemical removal. The self-indicating colorimetric response materials can be used to detect/sense toxic chemicals via liquid, solid, and/or gas/vapor phase exposure. The compositions, methods, and devices provided by the invention are applicable to several fields including catalysis, decontamination, sensing, detection, separations, gas storage, and others. The provided compositions may be incorporated into films, wearable chemical sensors, chemical detection devices, or used in respirators and/or collective protection filters for use as end-of-service life indicators (ESLI) and/or residual life indicators (RLI). Exemplary devices employing the invention alert a user to when it is time to change-out the filter.

BACKGROUND OF THE INVENTION

Air purification, including individual and collective protection filtration, is of major concern to the military, first responders, and industrial workers. Filters typically containing activated, impregnated carbons are employed to filter toxic chemicals, and have limited lifetimes after exposure. Furthermore, due to interaction with environmental contaminants, such as low level concentrations of $SO_x$, $NO_x$, hydrocarbon vapors, etc., the capacity of filters can degrade even before a toxic chemical event.

Colorimetric sensing of toxic chemicals, such as chemical warfare agents and narcotics, is of major concern to the Department of Defense community, military, and first responders. In-place chemical sensors, such as M8 or M9 paper and the volatile organic compounds (VOC) test kit, can identify neat toxic chemicals, or more specifically chemical warfare agents, in the liquid phase only.

In individual protection having an end-of-service-life indicator (ESLI) that tells the user when the filter has run out of protective capability is a major development thrust, and a need for the community. Here, an ESLI should interact/react with toxic chemicals such that a response (ideally visible, but not necessarily) occurs. There are ESLI technologies currently being fielded; however, there are severe shortcomings to these, such as poor sensing of reactive gases or insufficient reactivity.

Due to continuous operation of filtration and sensing devices, ambient and battlefield contaminants (BFCs) decrease physical adsorption and chemical reactivity of the filter material over time due to interactions with the active sites associated with the material contained within the devices. Interactions can also occur with the pore structure and/or the impregnants associated with the filter material contained within the filter housing, such as for example activated carbon impregnated with salts of copper, zinc, molybdenum and silver, plus triethylenediamine. Residual life indicator (RLI) technologies have been developed; however, most do not accurately determine the effects of acidic/acid-forming contaminants on the residual life of the filtration media.

As such, new processes are needed for the detection and quantification of acidic/acid-forming contaminants that may be employed to determine the residual life of a filtration system.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The present invention describes processes for sensing a variety of toxic chemicals and/or processes for determining the residual life of a filter or filtration system.

The present invention also describes processes for films incorporating the self-indicating colorimetric response materials; wearable self-indicating colorimetric response chemical sensors; solid, liquid, and vapor chemical detection via real-time colorimetric response; and/or toxic chemical detection devices, such as optical, spectral, and/or electronic chemical sensors.

Processes for sensing a toxic chemical include: contacting a toxic chemical or a byproduct thereof with a transition metal reactant or cation reactant, optionally salts, oxides, nitrates, or oxyhydroxides of cobalt, copper, iron, manganese, or nickel and detecting the toxic chemical by determining a difference between the pre-exposure colorimetric state of the transition metal reactant or cation reactant and the post-exposure colorimetric state of the transition metal reactant or cation reactant. In some aspects, a transition metal or cation reactant includes $KMnO_4$, $CoCl_2$, $Co(NO_3)_2$, $CoSO_4$, $Co(C_2H_3O_2)$, $CuSO_4$, $CuBr$, $CuCl_2$, $Cu(NO_3)_2$, $Ni(NO_3)_2$, $NiCl_2$, $Fe(NO_3)_2$, $FeCl_2$, $FeCl_3$, $FeSO_4$, or combinations thereof. The processes also include the use of sorbents for removing and detecting toxic chemicals, wherein the sorbent comprises a porous metal oxide/hydroxide and a transition metal or cation reactant suitable to react with a toxic chemical or byproduct thereof and obtaining a pre-exposure colorimetric state of said sorbent and a post-exposure colorimetric state of said sorbent and detecting or sensing the toxic chemical based on a difference between the pre-exposure colorimetric state and post-exposure colorimetric state. A sorbent includes a porous mixed-metal oxide/hydroxide, where the porous mixed-metal oxide/hydroxide includes more than one metal. For example, a porous silicon-aluminum oxide/hydroxide wherein the silicon-to-aluminum ratio is 30, the metal oxide/hydroxide being reactive on the surface and within the porous structure that contacts the toxic chemical or byproduct thereof. The processes are suitable for detecting exposure to a variety of toxic chemicals with a variety of chemistries, optionally including, but not limited to ammonia, arsine, chlorine, cyanogen chloride, hydrogen chloride, hydrogen cyanide, hydrogen sulfide, methyl bromide, nitrogen dioxide, phosgene, sulfur dioxide, sulfur dichloride, 2-chloroethyl ethyl sulfide (2-CEES), fentanyl, remifentanil, carfentanil, chemicals containing thiolate leaving group, chemicals containing a chloride leaving group, chemicals containing a fluoride leaving group, chemicals containing a cyanide leaving group, or combinations thereof. In addition, the processes are suitable for detecting solid, liquid, and vapor exposure to a variety of toxic chemicals with a variety of chemistries, optionally including, but not limited to chemical warfare agents and narcotics such as fentanyls. The sorbent includes a porous metal or mixed-metal oxide/hydroxide, optionally a zeolite material with a silicon to aluminum metal-to-metal ratio of 30 which includes such metals as silicon, aluminum, titanium, and phosphorus within the framework exhibiting the beta, chabazite, and pentasil crystal structures. The metal oxide/hydroxide can exhibit but not be limited to a tetragonal, monoclinic, or triclinic crystal systems, where the space groups are P422, P1m1, and P-1. The sorbent includes a metal oxide/hydroxide, optionally an oxide/hydroxide of silicon, aluminum, magnesium, cobalt, copper, zinc, titanium, zirconium, vanadium, molybdenum, tungsten, niobium, tantalum, lithium, chromium, manganese, nickel, calcium, or mixtures thereof. In some aspects, a porous metal oxide/hydroxide is aluminum oxide/hydroxide, iron oxide/hydroxide, zinc oxide/hydroxide, silicon oxide/hydroxide, magnesium oxide/hydroxide, zirconium oxide/hydroxide, cobalt oxide/hydroxide, copper oxide/hydroxide, titanium oxide/hydroxide, molybdenum oxide/hydroxide, tungsten oxide/hydroxide, niobium oxide/hydroxide, tantalum oxide/hydroxide, lithium oxide/hydroxide, vanadium oxide/hydroxide, chromium oxide/hydroxide, manganese oxide/hydroxide, nickel oxide/hydroxide, calcium oxide/hydroxide, iron-silicon oxide/hydroxide, iron-aluminum oxide/hydroxide, silicon-aluminum oxide/hydroxide, silicon-aluminum-titanium-phosphorus oxide/hydroxide, or combinations thereof. If the mixed-metal oxide/hydroxide comprises more than two metals, for example, silicon-aluminum-titanium-phosphorus oxide/hydroxide, it is preferable the silicon-to-aluminum ratio is from 3 to 1,000 and preferably 30, the silicon-to-titanium ratio is from 2 to 500 and preferably 2, and the titanium-to-phosphorus ratio is from 1 to 500 and preferably 15. A sorbent optionally does not include pure aluminum silicates or zeolites exhibiting the beta, chabazite, or pentasil crystal structures. A sorbent optionally does not include pure zirconium hydroxide where pure zirconium hydroxide is zirconium hydroxide that is not in a mixed metal hydroxide form. In some aspects, a porous metal hydroxide optionally excludes pure zirconium hydroxide, zirconium hydroxide in a mixed metal hydroxide, or both. These sorbents include or incorporate a transition metal or cation reactant, optionally salts, oxides, nitrates, or oxyhydroxides of cobalt, copper, iron, manganese, or nickel. In some aspects, a transition metal or cation reactant includes $KMnO_4$, $CoCl_2$, $Co(NO_3)_2$, $CoSO_4$, $Co(C_2H_3O_2)$, $CuSO_4$, $CuBr$, $CuCl_2$, $Cu(NO_3)_2$, $Ni(NO_3)_2$, $NiCl_2$, $Fe(NO_3)_2$, $FeCl_2$, $FeCl_3$, $FeSO_4$, or combinations thereof. A transition metal or cation reactant is optionally present in the sorbent at a concentration of 1 to 90 weight percent. In some aspects, a sorbent further includes a dye, optionally bromophenol blue. Optionally, a dye is absent. In some aspects, a sorbent includes a hydrolysis additive, optionally triethylenediamine (TEDA). Optionally, a hydrolysis additive is excluded. Any of the sorbents in any combination is optionally included within or coated on a film forming polymer. The polymer may also be porous. A film forming polymer optionally includes a functional group selected from the group consisting of alkanes, alkenes, alkynes, amines, alcohols, acids, ethers, esters, anhydrides, amides, nitriles, aromatic rings, isocyanates, and azides. The sorbent may be combined with the film forming polymer prior to, during, or following polymerization of the film forming polymer. A sorbent is optionally combined with the film forming polymer by spray coating, dip coating, solvent casting, painting, thermal spray coating/powder coating, or spin coating. It is appreciated that the various aspects are combinable in many different ways as is appreciated by one of ordinary skill in the art in view of the present disclosure.

A sorbent can be integrated into a wearable chemical sensor, e.g. circuit with interdigitated capacitor (IDC) technology, or a film to swipe for toxic chemicals. As a film, the sorbent can also be used as a flexible colorimetric indicator for confirming toxic gas leaks. The sorbent can be composed of the metal or mixed-metal oxide/hydroxide, polymer, transition metal or cation reactant, or combination thereof. The sorbent can be fabricated, deposited, or spray-coated on suitable substrates, such as silica, fabrics, various surfaces such as panels, cement, glass, sand, asphalt, drywall, wood, adhesive substrates, or insulating, semi-conducting, or conducting substrates.

The colored transition metal reactants can also be incorporated into a system for camouflage applications for the military such as the Army, Navy, etc., due to their different hues of green, brown, and blue colors. Such materials include: $LiZn_{0.9}Co_{0.1}VO_4$, $Zn_{2-x}Ni_xMO_4$ (M=Zr, Ti; x=0.05-0.3), $Zn_{1-x}Cu_xAO_4$ (A=W, Mo; x=0.05-0.2), $Zn_{1.8}Cu_{0.2}TiO_4$, $Zn_{1.8}Co_{0.2}TiO_4$, $Zn_{1.8}Mn_{0.2}TiO_4$, $Zn_{0.9}Ni_{0.1}(VO_4)_2$, $Co_2TiO_4$, $Ni_2TiO_4$, $NiCoZrO_4$, $CuCoZTO_4$, $CuNiZrO_4$, $CuNiTiO_4$, $CoWO_4$, $NiWO_4$, $CuWO_4$, $MnWO_4$, $FeWO_4$, $ZnCuWO_4$, $Zn_{0.9}Co_{0.1}WO_4$, $ZnCoMO_4$ (M=Ti, Zr), $Zn_{1-x}Ni_xAO_4$ (A=W, Mo; x=0.05-0.3), $Zn_{1-x}Mn_xAO_4$ (A=W, Mo; x=0.05-0.3), but not limited to. Synthesized $CoMoO_4$ and $Zn_{0.9}Co_{0.1}MoO_4$ showed the color purple, and thus, these oxides could be used as a color indicator for filtration or RLI applications.

A sorbent is optionally provided as a portion of an in-service filter/filtration system. Such system optionally includes a sorbent of any of the multiple configurations recited herein and combinations thereof as is readily envisioned. An in-service filter/filtration system includes a filter housing and a sorbent within at least a portion of said filter housing, said sorbent comprising a porous metal or mixed-metal oxide/hydroxide, preferably where the porous mixed-metal oxide/hydroxide has certain metal-to-metal ratios, for example, 30 or 30-2-15, and a transition metal or cation reactant suitable to react with a toxic chemical or byproduct thereof. The sorbent is optionally located in the filter housing distal from an exposure surface. Such a configuration allows for detection of a toxic chemical that is no longer filtered by other filter material thereby sensing the end of filter lifetime. A detector or portion thereof is optionally included within the filter housing in electromagnetic contact with the sorbent. The sorbent includes a metal oxide/hydroxide, optionally an oxide/hydroxide of silicon, aluminum, magnesium, cobalt, copper, zinc, titanium, phosphorus, zirconium, vanadium, chromium, manganese, nickel, calcium, or mixtures thereof. In some aspects, a porous metal oxide/hydroxide is aluminum oxide/hydroxide, iron oxide/hydroxide, zinc oxide/hydroxide, silicon oxide/hydroxide, magnesium oxide/hydroxide, zirconium oxide/hydroxide, cobalt oxide/hydroxide, copper oxide/hydroxide, titanium oxide/hydroxide, molybdenum oxide/hydroxide, tungsten oxide/hydroxide, niobium oxide/hydroxide, tantalum oxide/hydroxide, lithium oxide/hydroxide, vanadium oxide/hydroxide, chromium oxide/hydroxide, manganese oxide/hydroxide, nickel oxide/hydroxide, calcium oxide/hydroxide, iron-silicon oxide/hydroxide, iron-aluminum oxide/hydroxide, silicon-aluminum oxide/hydroxide, silicon-aluminum-titanium-phosphorus oxide/hydroxide, or combinations thereof, where the porous mixed-metal oxide/hydroxide may have a metal-to-metal ratio of 30 (silicon-to-aluminum) or 30-2-15 (silicon-to-aluminum; silicon-to-titanium; titanium-to-phosphorus). A sorbent optionally does not include pure aluminum silicates or zeolites exhibiting the beta, chabazite, or pentasil crystal structures. A sorbent optionally does not include pure zirconium hydroxide where pure zirconium hydroxide is zirconium hydroxide that is not in a mixed metal hydroxide form. In some aspects, a porous metal hydroxide optionally excludes pure zirconium hydroxide, zirconium hydroxide in a mixed metal hydroxide, or both. A sorbent optionally further includes a transition metal or cation reactant, optionally salts, nitrates, oxides, or oxyhydroxides of cobalt, copper, iron, manganese, or nickel. In some aspects, a transition metal reactant includes $KMnO_4$, $CrCl_2$, $Cr(NO_3)_2$, $CoCl_2$, $Co(NO)_2$, $CoSO_4$, $Co(C_2H_3O_2)$, $CuSO_4$, $CuBr$, $CuCl_2$, $Cu(NO_3)_2$, $Ni(NO_3)_2$, $NiCl_2$, $FeCl_2$, $FeCl_3$, $FeSO_4$, or combinations thereof. A transition metal or cation reactant is optionally present in the sorbent at a concentration of 1 to 90 weight percent. In some aspects, a sorbent further includes a dye, optionally bromophenol blue. Optionally, a dye is absent. In some aspects, a sorbent includes a hydrolysis additive, optionally triethylenediamine (TEDA). Optionally, a hydrolysis additive is excluded. Any of the sorbents in any combination is optionally included within or coated on a film forming polymer. The polymer may be porous. A film forming polymer optionally includes a functional group selected from the group consisting of alkanes, alkenes, alkynes, amines, alcohols, acids, ethers, esters, anhydrides, amides, nitriles, aromatic rings, isocyanates, and azides. The sorbent may be combined with the film forming polymer prior to, during, or following polymerization of the film forming polymer. A sorbent is optionally combined with the film forming polymer by spray coating, dip coating, solvent casting, painting, thermal spray coating/powder coating, or spin coating. It is appreciated that the various aspects are combinable in many different ways as is appreciated by one of ordinary skill in the art in view of the present disclosure.

DETAILED DESCRIPTION OF EMBODIMENTS OF THE INVENTION

Figure 1:
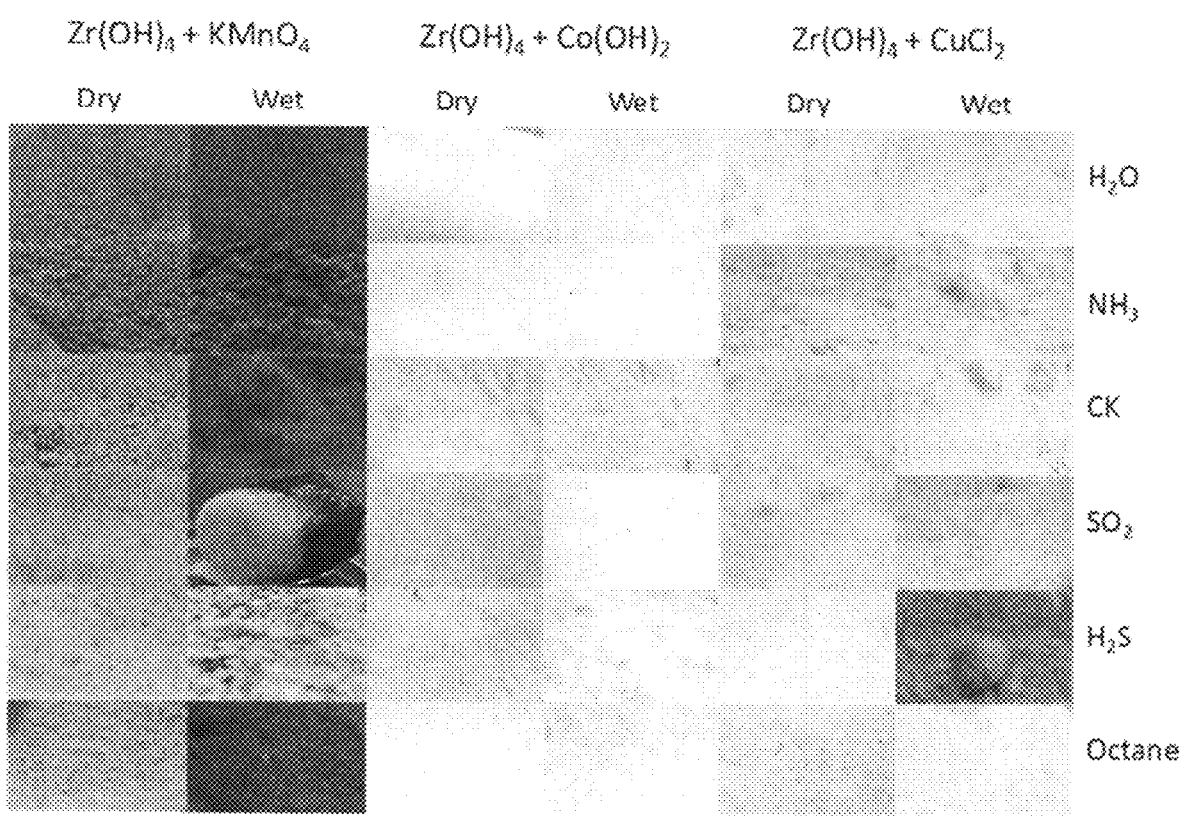
FIG. 1 illustrates the colorimetric changes of various sorbents following exposure to an array of toxic chemicals.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions are described as using specific materials in a particular order, it is appreciated that the described materials or order may be interchangeable such that the description of the invention includes multiple parts or steps arranged in many ways as is readily appreciated by one of skill in the art.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Ambient and battlefield contaminants such as sulfur dioxide ($SO_2$), nitrogen dioxide ($NO_2$), acid forming chemicals such as hydrogen chloride (HCl), and heavy organic vapors can detrimentally affect filter capacity for toxic chemicals. Provided are processes and materials that create a sensitive and robust response to these and similar chemicals to be useful to determine the residual capacity of in-service filters.

Chemical detection or sensing of vapor, liquid, and solid toxic chemicals such as chemical warfare agents and their by-products via self-indicating colorimetric response is of strong interest to the Department of Defense community. To date, there have been no reports showing colorimetric detection of both toxic chemical vapor and solid detection. Thus, having the capability to identify a class of CWAs or chemicals containing a specific leaving group via vapor or liquid chemical detection helps address a gap to the community to develop the next generation of chemical detectors. Provided are processes and materials that create a selective and robust response to these and similar chemicals.

Pure zeolite materials, which are white porous materials, have shown precedent for the decontamination of CWAs. However, no work has been shown for the decontamination of CWAs and/or self-indicating colorimetric response to CWAs or their by-products through the incorporation of transition metal reactants or cations into the framework.

Beyond actual filtration of toxic chemicals, it was discovered that porous metal hydroxides may be useful as a substrate for adding other metals, metal salts, and/or metal oxyhydroxides that will change color upon contact with toxic vapors. Zirconium hydroxide, as one example of a porous metal hydroxide when properly prepared, is a white amorphous material containing a combination of acidic and basic hydroxyl groups on the surface, which lend to its reactivity. Various substrates of porous metal hydroxides exist and are dependent on the method of precipitation and/or synthesis. Thus, a variety of materials are possible, with large deviations in surface area (such as for example 200-500 $m^2/g$) and porosity (such as for example pore volume between about 0.2-1.0 cc/g) possible.

Metal salts that interact with toxic chemicals or byproducts of reaction between toxic gases and a porous metal hydroxide may result in a color change. This color change is thus an indication that a toxic gas is present, and therefore acts as a sensor. This may be useful as a sensor array to detect a variety of gases, as a residual life indicator (RLI) that acts as a dosimeter, or as an end-of-service-life (ESLI) indicator, which illustrates a breakthrough wave or toxic chemical traversing through a filter.

For a porous metal hydroxide, the typical byproduct from acidic/acid-forming gases will be a hydrolysis product. Several examples are shown below. In some cases, more basic conditions are required, and are provided by the metal oxide surface or other additives.

Cyanogen chloride (CK): $CNCl+H_2O \rightarrow HOCN+HCl$

Chlorine: $Cl_2+H_2O \rightarrow HOCl+HCl$

Phosgene: $COCl_2+H_2O \rightarrow CO_2+2HCl$

Other chemicals may be oxidized. This may occur on the surface of porous metal hydroxide or with another metal additive, such as $KMnO_4$, Ag, Cu, or other oxidizing metal species.

Sulfur dioxide: $SO_2+\frac{1}{2}O_2+H_2O \rightarrow H_2SO_4$

Arsine: $2AsH_3+3O_2 \rightarrow As_2O_3+3H_2O$

Hydrogen sulfide: $H_2S+\frac{1}{2}O_2 \rightarrow S^0+H_2O$

Many metals will react with byproducts or chemicals themselves through simple interactions. For example, metal sulfates may interact with hydrogen chloride byproducts to form the corresponding metal chloride. Oxidizing species, such as $KMnO_4$, will oxidize chemicals such as sulfur dioxide, arsine, and hydrogen sulfide, reducing the manganese to yield a color change from a brilliant purple to a dull brown or lighter purple.

The provided processes use porous metal hydroxides, such as for example zirconium hydroxide, aluminum hydroxide, iron hydroxide, etc. in combination with additional metals, metal oxyhydroxides, and/or metal salts to react with and sense the presence of a toxic chemical(s) or toxic chemical by-products. Other metal hydroxides include porous metal oxide/hydroxide such as aluminum oxide/hydroxide, iron oxide/hydroxide, zinc oxide/hydroxide, silicon oxide/hydroxide, magnesium oxide/hydroxide, zirconium oxide/hydroxide, cobalt oxide/hydroxide, copper oxide/hydroxide, titanium oxide/hydroxide, molybdenum oxide/hydroxide, tungsten oxide/hydroxide, niobium oxide/hydroxide, tantalum oxide/hydroxide, lithium oxide/hydroxide, vanadium oxide/hydroxide, chromium oxide/hydroxide, manganese oxide/hydroxide, nickel oxide/hydroxide, calcium oxide/hydroxide, and mixed-metal oxides/hydroxides such as iron-silicon oxide/hydroxide, iron-aluminum oxide/hydroxide, silicon-aluminum oxide/hydroxide, silicon-aluminum-titanium-phosphorus oxide/hydroxide, or combinations thereof. A sorbent includes a porous mixed-metal oxide/hydroxide, where the porous mixed-metal oxide/hydroxide includes more than one metal. For example, a porous silicon-aluminum oxide/hydroxide wherein the silicon-to-aluminum ratio is 30, the metal oxide/hydroxide being reactive on the surface and within the porous structure that contacts the toxic chemical or byproduct thereof. If the mixed-metal oxide/hydroxide comprises more than two metals, for example, silicon-aluminum-titanium-phosphorus oxide/hydroxide, it is preferable the silicon-to-aluminum ratio is from 3 to 1,000 and most preferably 30, the silicon-to-titanium ratio is from 2 to 500 and most preferably 2, and the titanium-to-phosphorus ratio is from 1 to 500 and most preferably 15. A sorbent optionally does not include pure aluminum silicates or zeolites exhibiting the beta, chabazite, or pentasil crystal structures. Illustrative examples of a toxic chemical by-product include but are not limited to HCl, HF, organic acid byproducts, and thiol byproducts. Toxic chemical by-products may also include adsorbed species, such as for example surface bound alkoxides, surface bound EMPA, etc, as described by Bandosz et al., *J. Phys. Chem C.*, 2012; 116:11606. A by-product as used herein is a natural or non-natural breakdown product of a toxic chemical. In some aspects, the processes relate to the use of porous metal hydroxides for sensing toxic industrial chemicals. This is accomplished based on the reactivity of the porous metal hydroxide substrate with acidic/acid-forming gases (as an example), and the added metal species changing color due to said interaction. In some aspects, there may be direct reactions with the added metal species. The provided process use transition metal compounds, such as for example transition metal nitrates, to react with and sense the presence of a toxic chemical(s), such as for example chemical warfare agents and its by-products. Processes are provided for sensing a toxic chemical such as an acidic/acid-forming and/or oxidizable gas including contacting a toxic chemical, or byproduct thereof, with a sorbent for a sampling time, the sorbent comprising a porous metal hydroxide and a transition metal reactant suitable to react with a toxic chemical or byproduct thereof, determining a difference between a post-exposure colorimetric state of said sorbent and a pre-exposure colorimetric state or said sorbent or control to thereby sense the presence or absence of the toxic chemical. As such, a "sorbent" as defined herein is a color-indicating material that will provide a change in colorimetric state upon contact with a toxic chemical or byproduct thereof.

Processes are provided for sensing a toxic chemical via solid, liquid, and/or vapor/gas phase chemical exposure with a sorbent for a sampling time. The sorbent can comprise a porous metal hydroxide, or a porous metal oxide/hydroxide, or preferably a porous mixed-metal oxide/hydroxide having certain metal-to-metal ratios, and a transition metal reactant or cation or transition metal compound suitable to react with a toxic chemical or by-product thereof, which exhibits a color change upon exposure to the toxic chemical. Determining a difference between post-exposure colorimetric state of said sorbent and a pre-exposure colorimetric state or said sorbent is thereby used to sense the presence or absence of the toxic chemical.

A process includes contacting a toxic chemical with a sorbent for a sampling time. The step of contacting may be by active pressure combination optionally including mixing, by passive contact, or by other mechanism. A sampling time may be any time from 0.1 seconds to 30 days or more, or any value or range between 0.05 seconds to 30 days. A sampling time is optionally 0.05 seconds to 24 hours, optionally 0.05 seconds to 1 hour, optionally 10 seconds to 20 minutes, optionally 1 minute to 20 minutes. A sampling time, in some aspects, is any time sufficient to show a detectable change in a colorimetric state.

A process further includes obtaining a post-exposure colorimetric state of the sorbent and optionally a determining a difference in a colorimetric state of the sorbent following the contacting step and determining the presence or absence of a difference in the colorimetric state relative to a pre-exposure colorimetric state or that of a control. Measuring or determining the colorimetric state of a material is optionally performed by one or more of many techniques known in the art. Illustratively, colorimetric state is determined by visual inspection. Optionally, a colorimetric state is determined using a spectrometer, optionally a Fourier transform infrared (FTIR) spectrometer, to determine colorimetric state of the sorbent at one or multiple wavelengths or ranges of wavelengths. Illustrative examples of such spectroscopic techniques can be found in Peterson, et al., *Industrial & Engineering Chemistry Research*, 2013; 53:701-707. Other illustrative methods for measuring or determining the presence or absence of a difference in colorimetric state include UV/Vis spectrometry, photoluminescence, luminescence, and fluorescence.

In some aspects, the post-exposure colorimetric state is used to determine or measure sorbent contact with a toxic chemical or byproduct thereof, and optionally to quantify the amount of toxic chemical or byproduct thereof that has contacted the sorbent by comparison to a pre-exposure colorimetric state or control. The contact of the sorbent with the toxic chemical or byproduct thereof can be made with the toxic chemical in the solid, liquid, or vapor/gas phase. A pre-exposure colorimetric state is measured prior to a sorbent contacting a toxic chemical or byproduct(s) thereof using the same techniques as are used for measuring a post-exposure colorimetric state. An altered colorimetric state indicates that the sorbent has contacted a toxic chemical or byproduct thereof. A colorimetric state is optionally altered in transmission at one or more wavelengths, reflection at one or more wavelengths, absorption at one or more wavelengths, or fluoresces or luminescence at one or more wavelengths. In some aspects, the post-exposure colorimetric state is compared to a control. A control is a colorimetric state of a pre-exposure sorbent similar or identical sorbent contacted with the toxic chemical or byproduct thereof. A difference between a post-exposure colorimetric state and a pre-exposure colorimetric state or control allows for the sensing or quantifying contact of a sorbent with a toxic chemical or byproduct thereof or other environmental condition.

A colorimetric state is a spectral condition of a sorbent. A colorimetric state is observable, and optionally quantifiable, visually or using instrumentation. A colorimetric state is observed as a color, a spectral pattern, an intensity of spectral emission(s), or combinations thereof. A colorimetric state is optionally observed at one or more wavelengths between the far infrared to far UV. Optionally, a colorimetric state is observed at or between a wavelength of 10 nm to 1 mm, or any value or range therebetween. In some aspects, a colorimetric state is observed within the visible spectrum of 390 to 700 nm. Optionally, a colorimetric state is observed at 5 μm to 25 μm. A difference in colorimetric state is observed by a relative change in a color or color spectra of the sorbent, either measured as absorbance, reflectance, fluorescence, or emission.

A toxic chemical is optionally an acidic/acid-forming and/or oxidizable gas, or a byproduct thereof. Many different acidic/acid-forming and/or oxidizable gases are detectable by the processes provided. Illustrative examples include such acidic/acid-forming and/or oxidizable gases as are used for defense or deterrent purposes, or those normally found in a battlefield scenario. Specific illustrative examples include, but are not limited to sulfur dioxide, octane, methyl bromide, hydrogen sulfide, cyanogen chloride, hydrogen cyanide, ammonia, nitrogen dioxide, hydrogen chloride, hydrogen chloride, HF, HBr, HCN, $Cl_2$, phosgene, boron trifluoride, boron trichloride, or combinations thereof.

A toxic chemical is optionally an amine. Illustrative examples of toxic amines include ethylamine, ammonia, among others.

A toxic chemical is optionally a hydride. Illustrative examples of hydride include arsine, phosphine, and the like.

A toxic chemical is optionally a chemical containing a thiolate leaving group, such as thiol.

A toxic chemical is optionally a chemical containing a cyanide leaving group, such as tabun.

A toxic chemical is optionally a chloride. Examples of chloride containing chemicals besides pure chlorine are sulfur dichloride, 2-CEES.

A toxic chemical is optionally a fluoride. Examples of fluoride containing chemicals include hydrogen fluoride, dimethyl fluoride, or any of G-class chemical warfare agents.

A toxic chemical is optionally a chemical warfare (CW) agent, including, e.g., toxic organophosphorus-type agents, mustard gas and derivatives, and similar such art-known toxins. Illustrative specific examples of CW agents, include but are not limited to bis-(2-chloroethyl)sulfide (HD or mustard gas), pinacolyl methylphosphonofluoridate (GD). Tabun (GA), Sarin (GB), cyclosarin (GF), and O-ethyl S-(2-diisopropylamino)ethyl methylphosphonothioate (VX), other toxic organophosphorus-type agents, their analogs or derivatives, and similar such art-known toxins.

In addition, unless otherwise stated, the term "toxic chemical" as used herein is also intended to include toxic industrial chemicals, including, but not limited to, organophosphorus-type insecticides, and the like. Mineral acids, such as for example hydrochloric acid solutions, sulfuric acid solutions, etc. are also exemplary toxic agents.

In some aspects, a toxic chemical is an aldehyde, optionally formaldehyde.

In some aspects a toxic chemical is a narcotic such as fentanyl.

Processes and systems use a sorbent. A sorbent is defined as including a material capable of reacting with a toxic chemical, absorbing a toxic chemical, or both. A sorbent includes a porous metal hydroxide. A porous metal hydroxide as defined herein is a metal hydroxide, mixed metal hydroxide, or mixtures thereof optionally having surface area(s) of or greater than 5 $m^2/g$, optionally of or greater than 10 $m^2/g$, optionally of or greater than 20 $m^2/g$, optionally of or greater than 30 $m^2/g$, optionally of or greater than 40 $m^2/g$, optionally of or greater than 50 $m^2/g$, optionally of or greater than 200 $m^2/g$, optionally of or greater than 500 $m^2/g$. In some aspects the pore volume of a porous metal hydroxide is at or greater than 0.1 $cm^3/g$, optionally at or greater than 0.25 $cm^3/g$, optionally at or greater than 0.5 $cm^3/g$.

A porous metal oxide/hydroxide optionally includes a reticular framework such as beta, pentasil, or chacabite structures.

A porous metal oxide/hydroxide optionally includes a metal to metal ratio of 30.

A porous metal oxide/hydroxide optionally includes a framework containing aluminum, silicon, phosphorus, and/or titanium or combination thereof.

A porous metal oxide/hydroxide optionally includes a metal or cation with a +1, +2, +3, +4, or +5 oxidation state. Illustrative non-limiting examples of porous metal hydroxides include aluminum hydroxide, iron hydroxide, zinc hydroxide, silicon hydroxide, magnesium hydroxide, cobalt hydroxide, copper hydroxide, titanium hydroxide, vanadium hydroxide, chromium hydroxide, manganese hydroxide, nickel hydroxide, calcium hydroxide, zirconium hydroxide and the like. In some aspects a metal hydroxide is not pure zirconium hydroxide where pure zirconium hydroxide is zirconium hydroxide that is not in a mixed metal hydroxide form. In some aspects, a metal hydroxide excludes pure zirconium hydroxide and zirconium hydroxide in a mixed metal hydroxide.

A porous metal hydroxide is optionally a mixed metal hydroxide. Illustrative examples of mixed metal hydroxides include but are not limited to metal hydroxides including two or more metals of aluminum, iron, zinc, silicon, magnesium, cobalt, copper, titanium, phosphorus, vanadium, chromium, manganese, nickel, calcium, zirconium, and the like. Specific illustrative examples of mixed metal hydroxides include iron-silicon hydroxide, iron-aluminum hydroxide, silicon-aluminum hydroxide, among others. The porosity associated with the porous metal hydroxide allows for absorption of the toxic chemical from the surface of a contaminated item into the pores of the reactive sorbent, where the toxic chemical will be decomposed.

The porous metal hydroxide optionally includes any metal hydroxide or multi-metal hydroxide, or mixture thereof that is capable of absorbing, or taking up harmful toxic materials including toxic chemicals, and optionally then catalytically or stoichiometrically reacting, converting, deactivating, neutralizing, or detoxifying at least a portion of the absorbed toxic chemical.

Properties of Exemplary Porous Metal Hydroxides:

In some aspects, a porous metal hydroxide has sufficient porosity so that it readily and rapidly absorbs one or more toxic chemicals in the form of either liquid or gas. The toxic chemical will be absorbed into the pore structure of the porous metal hydroxide. In some aspects, the surface area is at or greater than about 50 $m^2/g$, optionally at or greater than 200 $m^2/g$, optionally at or greater than 500 $m^2/g$. In some aspects, the pore volume of the porous metal hydroxide is at or greater than 0.1 $cm^3/g$, optionally at or greater than 0.25 $cm^3/g$, optionally at or greater than 0.5 $cm^3/g$.

In some aspects, the porous metal hydroxide has a very low solubility in water, such as for example solubility less than 0.1 g per 100 ml of water. Should moisture be excessive, a water soluble porous metal hydroxide will begin to dissolve, forming a thick paste-like substance that may reduce the efficacy of the sorbent. Further, highly water soluble metal hydroxides, such as sodium hydroxide and potassium hydroxide, are highly corrosive and should be avoided.

The porous metal hydroxide may be of several geometric forms. Said forms include beads, spheres, granules, powders, etc. and may be prepared using techniques known to one skilled in the art. Small beads or bead-like geometries, such as that prepared by spray drying processes as known in the art, for example, are preferred in some aspects. This is because beads and bead-like geometries will readily flow across the surface, optimizing the time required to perform the process. Particles having a linear cross sectional dimension on the order of about 5 nm to 100 μm may be used, optionally 50 nm to 100 μm, optionally 100 nm to 100 μm, optionally 500 nm to 100 μm, optionally 5 nm to 99 μm, optionally 5 μm to 100 μm, 5 μm to 99 μm, optionally 5 μm to about 80 μm.

Exemplary Sorbent Preparation

Porous metal hydroxides can be prepared via precipitation routes as known by one skilled in the art. Porous metal hydroxides may be precipitated by contacting a soluble form of the metal with an acidic or alkaline solution in a manner which alters the pH of the solution such as to bring about precipitation. For example, aluminum hydroxide may be prepared by contacting an aluminum solution, such as for example one prepared using sodium aluminate dissolved in sodium hydroxide, with an acidic solution, such as for example sulfuric acid at a pH sufficient to bring about precipitation. While not wishing to be bound by any theory, one possible reaction pathway by which precipitation leading to the formation of aluminum hydroxide occurs is as follows:

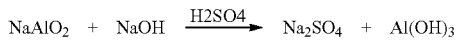

Aluminum hydroxide can also be prepared using aluminum nitrate according to:

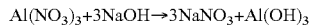

Other porous metal hydroxides, such as those involving magnesium, aluminum, silicon, calcium, titanium, iron, cobalt, nickel, copper, zinc and zirconium, or co-precipitated solids thereof, or mixtures thereof, can be prepared via similar techniques. Soluble forms of magnesium include magnesium chloride, magnesium sulfate and magnesium nitrate, for example. Soluble forms of aluminum include sodium aluminate and aluminum nitrate, for example. Soluble forms of silicon include sodium silicate and colloidal silica solutions, for example. Fumed silicas can also be digested or partially digested in sodium hydroxide solutions. Soluble forms of calcium, iron, cobalt, nickel, copper and zinc include the corresponding nitrates, sulfates and chlorides, for example. Soluble forms of titanium include titanium sulfate. Soluble forms of zirconium include zirconium oxynitrate and zirconium oxychloride, for example.

If the soluble form of the metal results in an acidic solution, alkali metal hydroxides, such as lithium hydroxide, sodium hydroxide and potassium hydroxide can be used to increase the pH of the solution, thereby bringing about the formation of the porous metal hydroxide via precipitation. Other bases, such as ammonium hydroxide, can also be used. If the soluble form of the metal results in a basic solution, mineral acids, such as sulfuric acid, hydrochloric acid and nitric acid, may be used to decrease the pH of the solution, thereby bringing about the formation of the porous metal hydroxide. Other acids, such as organic acids of which formic acid is included, may also be used.

Mixed or co-precipitated porous metal hydroxides may also be prepared. For example, a co-precipitated iron-silicon hydroxide may be prepared by combining an alkaline sodium silicate solution with an acidic iron chloride solution to bring about the formation of a porous iron-silica hydroxide. Said solutions can also contain excess alkali or acids so that the relative amounts of each metal in the porous metal hydroxide may be allowed to vary.

When forming the porous metal hydroxide, structure directing agents may be added to the precipitation solution to enhance the porosity. Examples of structure directing agents include, but are not limited to glycols, ethers, quaternary ammonium salts, and the like. Examples of glycols include polyethylene glycol and polypropylene glycol. Examples of ethers include dimethyl ether and diethyl ether. Examples of quaternary ammonium salts include tetrapropylammonium bromide and tetrabutulammonium bromide. The use of structure directing agents can greatly affect the porosity of the resulting porous metal hydroxide.

Once precipitation is complete, the porous metal hydroxide is optionally washed with water to remove any dissolved salts or structure directing agent from the pore structure, then dried. Drying is a key step in the operation, as at too high of temperature, the porous metal hydroxide will begin to decompose to the corresponding oxide. Decomposition will decrease the porosity of the resulting solid plus remove hydroxyl groups necessary to facilitate reactions related to detoxification. Ideally, the porous metal hydroxide is dried at temperatures below about 150° C., although higher temperatures and short durations may be employed. The upper temperature limit employed in the drying operation will depend upon the composition of the porous metal hydroxide.

Such processes optionally produce a porous metal hydroxide that is substantially pure. The term substantially pure is meant free of additional contaminating metals, salts, acids, or other materials that may detract from the effectiveness of the resulting porous metal hydroxide. Substantially pure optionally means 90% pure, optionally 91% pure, optionally 92% pure, optionally 93% pure, optionally 94% pure, optionally 95% pure, optionally 96% pure, optionally 97% pure, optionally 98% pure, optionally 99% pure, optionally 99.1% pure, optionally 99.2% pure, optionally 99.3% pure, optionally 99.4% pure, optionally 99.5% pure, optionally 99.6% pure, optionally 99.7% pure, optionally 99.8% pure, optionally 99.9% pure, or of greater purity.

A sorbent optionally further includes a porous metal hydroxide loaded with or otherwise containing one or more transition metal reactants. A transition metal reactant is a transition metal component capable of reacting with a toxic chemical or a byproduct thereof. In some aspects, a transition metal reactant includes salts, oxides, hydroxides, or oxyhydroxides of cobalt, copper, iron, manganese, or nickel. Specific illustrative examples of a transition metal reactant include $KMnO_4$, $CoCl_2$, $Co(NO_3)_2$, $CoSO_4$, $Co(C_2H_3O_2)$, $CuSO_4$, $CuBr$, $CuCl_2$, $Cu(NO_3)_2$, $NiCl_2$, $FeCl_3$, $FeSO_4$.

A transition metal reactant is included in a sorbent at a concentration sufficient to react with a toxic chemical or byproduct thereof. Optionally, a transition metal reactant is present at 1 to 50 weight percent of the sorbent. In some aspects, a transition metal reactant is present at a weight percent of 1 to 40, optionally 1 to 30, optionally 1 to 20, optionally 1 to 19, optionally 1 to 18, optionally 1 to 17, optionally 1 to 16, optionally 1 to 15, optionally 1 to 14, optionally 1 to 13, optionally 1 to 12, optionally 1 to 11, optionally 1 to 10, optionally 1 to 9, optionally 1 to 8, optionally 1 to 7, optionally 1 to 6, optionally 1 to 5, optionally 2 to 10, optionally 5 to 10.

A porous metal hydroxide optionally includes or is free of one or more additional reactive moieties. A porous metal hydroxide optionally includes or is free of a reactive moiety either adsorbed to the surface of the porous metal hydroxide, impregnated into the porous metal hydroxide, or co-precipitated with the porous metal hydroxide. Illustratively, a porous metal hydroxide optionally includes or is free of one or more reactive, catalytic, or functional groups (in sum "reactive moiety"). Illustrative examples of reactive, catalytic, or functional groups include base metals or amines. A base metal is optionally vanadium, chromium, manganese, iron, cobalt, nickel, copper, zinc, silver, molybdenum, and mixtures thereof. When present, a base metal is optionally in the amount of about 5% to about 40% by weight of the sorbent, optionally at or about 15% to about 25%.

A reactive, catalytic, or functional group is optionally an amine. Illustrative examples of an amine include triethylamine (TEA), quinuclidine (QUIN), triethylenedianmine (TEDA), pyridine, and pyridine carboxylic acids such as pyridine-4-carboxylic acid (P4CA). The loading of an amine, illustratively TEDA, is optionally as low as 0 wt. %, or as high as about 6 wt. %. Optionally an amount of amine, illustratively TEDA, used is of from about 3% to about 6% by weight of the sorbent.

Illustrative examples of methods for the incorporation of reactive, catalytic, or functional group(s) into a hydroxide are found in U.S. Pat. No. 8,530,719.

A sorbent optionally further includes a fluorescent material. A fluorescent material may be, but is not limited to a lanthanide. Compared to organic fluorescent molecules, lanthanides have a longer fluorescent lifetime, they have a large stokes shift such that excitation at a wavelength of 310-350 nm, optionally 340 nm, produces emissions of these molecules in the visible spectrum, and in many instances the FWHM is quite sharp, often of 10 nm or less. These characteristics of fluorescently labeled metal oxyhydroxide improve the sensitivity of the inventive processes. Illustrative examples of fluorescent lanthanides include $Eu^{3+}$, $Tb^{3+}$, $Sm^{3+}$, $La^{3+}$, and $Dy^{3+}$. A metal oxyhydroxide is optionally doped by a fluorescent material by processes known in the art, illustratively by the process described in Bouznit, et al., *Appl. Surf. Sci.*, 2012; 258:2967-2971 or Sun, et al., *J. Materials Chem.*, 2012; 22:8221-8227.

A sorbent may be provided in one or more of many forms. Illustratively, a sorbent may be provided in the form of a powder, granule, particle, or film. In some aspects, a sorbent is combined with one or more polymeric materials to form a film. A polymeric material optionally includes a polymer and optional cross linker. A polymer is optionally any film-forming polymer useful in coating compositions. Such polymers illustratively include aminoplasts, melamine formaldehydes, carbamates, polyurethanes, polyacrylates, epoxies, polycarbonates, alkyds, vinyls, polyamides, polyolefins, phenolic resins, polyesters, polysiloxanes, and combinations of any of these or other polymers.

In some aspects, a polymer is crosslinkable. For example, a crosslinkable polymer has a functional group characteristic of a crosslinkable polymer. Examples of such functional groups illustratively include acetoacetate, acid, amine, carboxyl, epoxy, hydroxyl, isocyanate, silane, and vinyl.

A polymeric material optionally includes a crosslinker. The particular crosslinker selected depends on the particular polymer used. Non-limiting examples of crosslinkers include compounds having functional groups such as isocyanate functional groups, epoxy functional groups, aldehyde functional groups, and acid functionality.

In particular aspects, sorbent-polyurethane composite materials is formed where a polymer is a hydroxyl-functional acrylic polymer and the crosslinker is a polyisocyanate.

A polyisocyanate, preferably a diisocyanate is a crosslinker reacted with the hydroxyl-functional acrylic polymer. Aliphatic polyisocyanates are preferred polyisocyanates used in processes for making protein-polymer composite materials for clearcoat applications such as in automotive clearcoat applications. Non-limiting examples of aliphatic polyisocyanates include 1,4-butylene diisocyanate, 1,4-cyclohexane diisocyanate, 1,2-diisocyanatopropane, 1,3-diisocyanatopropane, ethylene diisocyanate, lysine diisocyanate, 1,4-methylene bis (cyclohexyl isocyanate), diphenylmethane 4,4'-diisocyanate, an isocyanurate of diphenylmethane 4,4'-diisocyanate, methylenebis-4,4'-isocyanatocyclohexane, 1,6-hexamethylene diisocyanate, an isocyanurate of 1,6-hexamethylene diisocyanate, isophorone diisocyanate, an isocyanurate of isophorone diisocyanate, p-phenylene diisocyanate, toluene diisocyanate, an isocyanurate of toluene diisocyanate, triphenylmethane 4,4',4"-triisocyanate, tetramethyl xylene diisocyanate, and meta-xylene diisocyanate.

In some aspects, a sorbent may be layered within, separate from, or intermixed with a filter material. In some aspects, a sorbent is placed in close proximity to a filter material, optionally contacting a filter material. Illustrative examples of a filter material include carbon such as ASZM-TEDA carbon. A sorbent may be placed at multiple locations within a bed of filter material such that as an acidic/acid-forming and/or oxidizable gas penetrates the filter material, it also comes into contact with the sorbent so that the metal oxyhydroxide may be used to detect the presence of or amount of an acidic/acid-forming and/or oxidizable gas that the filter material has been exposed to. Such an arrangement may detect a wavefront or exposure front of a gas.

In some aspects, the processes are capable of detecting exposure of an environmental challenge such as an acidic/acid-forming and/or oxidizable gas that has contacted the sorbent by change(s) in the post-exposure colorimetric state relative to a pre-exposure colorimetric state or control. Either using a sorbent alone or by embedding the sorbent in a bed of filtration material uniformly or at one or more discrete locations allows for monitoring bed exposure to an environmental challenge. As one illustrative example, exposure of a toxic chemical to a first area of a filter bed will alter the color or other spectral property of the exposed area while an area of the bed that is more distant from the front face (most exposed) of the filter bed may continue to register unexposed. This would indicate that the filter material has residual life in still being able to perform as expected. Additional exposure to an acidic/acid-forming and/or oxidizable gas as an exemplary environmental challenge, will cause an area of the bed more distal from the front face of the filter material to show a colorimetric state change indicating additional exposure and less residual life to the filtration media. When an area of the bed shows a colorimetric change due to exposure such that an insufficient amount of unexposed filtration media remains, the filter media has reached the end of its useful lifetime. As such, the processes may be used to determine the residual life of the filter material.

As such, processes are provided for determining the residual capacity (lifetime) of an in-service filter or filtration system. Such processes include optionally depositing one or more sorbents within a filter material such as by embedding within one or more portions of filter material, placing the sorbent on a swatch of material, or otherwise locating one or more sorbents within or adjacent to a filter material; contacting a toxic chemical or byproduct thereof with the sorbent for a sampling time; obtaining a post-exposure colorimetric state of the sorbent; and determining said residual capacity by comparing the post-exposure colorimetric state to a pre-exposure colorimetric state or control.

A sorbent is optionally located in a satellite location to the filter where the satellite location is expected to experience the same challenge by toxic chemical as is to be experienced by a relative filter material. Optionally, a sorbent is located directly adjacent to a filter material. In some embodiments, a sorbent is located at one or several locations embedded within a filter material. Embedding the sorbent in the filter material at various locations allows the monitoring of an exposure front from one surface of a filter to another. As one example presented for illustration only and not as a limitation, a 2 cm thick carbon filter may have two locations of sorbent embedded therein. Exposure to toxic chemical may affect the forward area of the filter material more than the rear area leaving effective filter material present at the rear of the filter. While the environmental challenge will have reduced the residual life of the filter material, the lower exposure of the area near the rear of the filter material will still be functional. Placing sorbent(s) at the various locations allows determination of how much fresh filter material remains.

Alternatively, in some aspects toxic chemical will irreversibly or irrevocably alter the filter material such that it is expected that a single exposure will be sufficient to destroy filter effectiveness. The singular detection of exposure by detecting the change in post-exposure colorimetric state of a sorbent relative to pre-exposure colorimetric state or control will indicate that no residual life is present in the filter.

Processes may be performed in situ or ex situ. For ex situ applications, the exposure of a sorbent may occur in a remote location and then transported to a detection location such as a lab (or mobile lab) to determine what chemical contaminants are present and optionally how much exposure the sorbent experienced. For in situ applications, exposure to a toxic chemical is optionally measured by a visual inspection or use of an instrument such as a spectrophotometer, fluorometer, or other instrument useful for detecting a colorimetric state of a sorbent. An instrument may be either separate from or integrated in part or in full within a filter or within the sorbent material itself.

A detection system could be miniaturized to fit into a wearable filter or filter system. The detector may be coupled to an alarm or other indicator controlled by the microprocessor to alert a user to the presence of a toxic chemical or to indicate that the filter is in need of replacement.

The processes provide reliable and reproducable detection of a toxic chemical such as the presence of one or more acidic/acid-forming and/or oxidizable gases or other toxic chemicals. Rapid determination may be made of the residual life of a filter material to which a sorbent is associated by detection of a shift in the wavelength of light absorbed or emitted at one or more wavelengths. By detection of a change in the relative intensities at one or more wavelengths of light in comparison to a pre-exposure colorimetric state or to a control, a user can quantify the amount of or identify the type of acidic/acid-forming and/or oxidizable gas or other toxic chemical the sorbent has been exposed to.

Various aspects of the present invention are illustrated by the following non-limiting examples. The examples are for illustrative purposes and are not a limitation on any practice of the present invention. It will be understood that variations and modifications can be made without departing from the spirit and scope of the invention. A person of ordinary skill in the art readily understands where any and all necessary reagents or materials may be commercially obtained.

EXAMPLES

Example 1: Preparation of Silicon Hydroxide 250 g of a sodium silicate solution (28% as silicon dioxide) was added to a 4 liter pail. To the solution was added 1.5 liters DI water. The solution was mixed for 15 minutes, then titrated to a pH of 7 using a 50% $H_2SO_4$ solution in order to bring about precipitation. The resulting slurry was mixed for 4 hours, then filtered. The product was washed twice with 3 liters of DI water, filtered, and then dried at 90° C. overnight. Product was ground to less than 40 mesh particles, a portion of which were dried at 90° C. to a moisture content of less than 3% water. The sample was placed in a glass jar and sealed. The surface area of the sample was 295 $m^2/g$. The pore volume of the sample was 0.804 $cm^3/g$. Particle size was less than 40 mesh.

Example 2: Preparation of Silicon Hydroxide Using Polyethylene Glycol

This example illustrates the effects of a structure directing agent on the porosity of precipitated metal hydroxides. 250 g of a sodium silicate solution (28% as silicon dioxide) was added to a 4 liter pail along with 25 g of polyethylene glycol (PEG—average molecular weight=1,450). To the solution was added 1.5 liters DI water and the solution was mixed until the PEG completely dissolved. Once dissolved, the solution was titrated to a pH of 7 using a 50% $H_2SO_4$ solution in order to bring about precipitation. The resulting slurry was mixed for 4 hours, then filtered. The product was washed twice with 3 liters of DI water, filtered, and then dried at 90° C. overnight. Product was ground to less than 40 mesh particles, a portion of which were dried at 90° C. to a moisture content of less than 3% water. The sample was placed in a glass jar and sealed. The surface area of the sample was 421 $m^2/g$. The pore volume of the sample was 0.682 $cm^3/g$. Particle size was less than 40 mesh.

Example 3: Preparation of Aluminum Hydroxide 250 g of a sodium aluminate solution (25% as aluminum oxide) was added to a 4 liter pail along with 25 g of polyethylene glycol (PEG—average molecular weight=1,450). To the solution was added 1.5 liters DI water and the solution was mixed until the PEG completely dissolved. Once dissolved, the solution was titrated to a pH of 7 using a 50% $H_2SO_4$ solution in order to bring about precipitation. The resulting slurry was mixed for 4 hours, then filtered. The product was washed twice with 3 liters of DI water, filtered, and then dried at 90° C. overnight. Product was ground to less than 40 mesh particles, a portion of which were dried at 90° C. to a moisture content of less than 3% water. The sample was placed in a glass jar and sealed. The surface area of the sample was 130 $m^2/g$. The pore volume of the sample was 0.13 $cm^3/g$. Particle size was less than 40 mesh.

Example 4: Preparation of Silicon-Aluminum Hydroxide 2.0 kg of sodium aluminate solution (25% $Al_2O_3$) was added to a 4 liter pail. To the solution was added 0.5 liters of DI water. To the solution was added 200 g of a sodium silicate solution (28% $SiO_2$) plus 100 g of a 50% NaOH solution. The pH of the slurry was then reduced to 7 using a 50% $H_2SO_4$ solution. The resulting gel was mixed for 3 hours, then filtered and washed twice with DI water. The solid precipitate was dried at 80° C. overnight. The material is 91.0% Al and 9.0% Si by weight. The surface area of the sample was 195 $m^2/g$. The pore volume of the sample was 0.25 $cm^3/g$. Particle size was less than 40 mesh.

Example 5: Preparation of Silicon-Aluminum Hydroxide

This batch was prepared using aluminum nitrate as both the aluminum source and precipitating agent. The material was prepared by adding 250 g of sodium silicate solution plus 1.5 liters DI water to a 4 liter pail. To the contents were added 25 g of tetrapropyl ammonium bromide as the structure directing agent plus 50 g of a 50% NaOH solution. A 60% aluminum nitrate solution was added to the slurry using a peristaltic pump. The $Al(NO_3)_3$ solution is 7.62% Al by weight. 216 g of solution were used to decrease the pH of the slurry to 8. The mixing was terminated following 4 hours and the slurry was allowed to stand overnight. The slurry was then filtered, then washed with DI water 3 times. The filtered product was then dried at 80° C. overnight. The material is 33.7% Al and 66.3% Si by weight. The surface area of the sample was 320 m$^2$/g. The pore volume of the sample was 0.59 cm$^3$/g. Particle size was less than 40 mesh.

Example 6: Preparation of Silicon-Aluminum Hydroxide

The material was prepared by adding 150 g of sodium silicate solution plus 75 mL of DI water to a round bottom flask. 10 g of tetrapropyl ammonium bromide and 7 g of a 50% NaOH solution were added slowly to the mixture. 5 g of aluminum nitrate solution was added to the slurry. The mixture was stirred overnight. The slurry was then vacuum filtered, and washed with DI water 3 times. The filtered product was placed in high density alumina crucibles and dried in a box furnace at 110° C. overnight. The material is 99.98% Si and 3.33% Al by weight; thus the silicon to aluminum metal molar ratio is 30. The BET surface area was 507 m$^2$/g. The pore aperture was 7 Å.

Example 7: Preparation of Silicon-Aluminum-Titanium Hydroxide

The material was prepared by adding 150 g of sodium silicate solution plus 75 mL of DI water to a round bottom flask. 10 g of tetrapropyl ammonium bromide and 7 g of a 50% NaOH solution were added slowly to the mixture. 5 g of aluminum nitrate solution was added to the slurry. 75 g of titanium (IV) oxide (anatase crystal structure) was added. The mixture was stirred overnight. The slurry was then vacuum filtered, and washed with DI water 3 times. The filtered product was placed in high density alumina crucibles and dried in a box furnace at 110° C. overnight. The material is 99.97% Si, 3.32% Al, and 49.97% Ti by weight. The silicon to aluminum molar ratio is 30, and the silicon to titanium molar ratio is 2. The BET surface area was 505 m$^2$/g. The pore aperture was 7 Å.

Example 8: Preparation of Silicon-Aluminum-Titanium-Phosphorus Hydroxide

The material was prepared by adding 150 g of sodium silicate solution plus 75 mL of DI water to a round bottom flask. 10 g of tetrapropyl ammonium bromide and 7 g of a 50% NaOH solution were added slowly to the mixture. 5 g of aluminum nitrate solution was added to the slurry. 75 g of titanium (IV) oxide (anatase crystal structure) was added. 5 g of crystalline phosphoric acid was slowly added to the slurry. The mixture was stirred overnight. The slurry was then vacuum filtered, and washed with DI water 3 times. The filtered product was placed in high density alumina crucibles and dried in a box furnace at 110° C. overnight. The material is 99.98% Si, 3.32% Al, 49.97% Ti, and 3.33% P by weight. The silicon to aluminum molar ratio, the silicon to titanium molar ratio, and the titanium to phosphorus ratio are 30, 2, and 15, respectively. The BET surface area was 534 m$^2$/g. The pore aperture was 6.8 Å.

Example 9: Preparation of Iron-Silicon Hydroxide 250 g of sodium silicate solution (28% SiO$_2$) was added to a 4 liter pail. To the solution was added 1 liter of DI water and 25 g of polyethylene glycol (average Molecular weight=1,450). The solution was mixed for 1 hour. An iron sulfate solution was prepared by dissolving 300 g FeSO$_4$.6H$_2$O in DI water (total volume=800 ml). 266 g of the iron sulfate solution was added to the slurry using a peristaltic pump in order to decrease the pH of the slurry to 7. Following 4 hours, mixing was terminated and the slurry was allowed to stand overnight. In the morning, the slurry was filtered, then washed twice with 3 liters of DI water. The final product was dried at 80° C. overnight. The composition was 33.1% Fe and 66.9% Si by weight. The surface area of the sample was 570 m$^2$/g. The pore volume of the sample was 0.47 cm$^3$/g. Particle size was less than 40 mesh.

Example 10: Preparation of Iron-Silicon Hydroxide

A precipitated iron/silica was prepared by dissolving 200 g of iron sulfate (20% iron) in 1 liter of DI water. To the solution was added 20 g of Polycat-41 as a structure directing agent. A second solution was prepared by diluting 825 g of Na$_2$SiO$_3$ solution (28% SiO$_2$) with 600 g of DI water. The sodium silicate solution as added the iron solution using a peristaltic pump. The entire amount of sodium silicate solution reduced the pH of the slurry to 7.65. The resulting slurry was blended for 4 hours, aged overnight, and then filtered. The solids were washed 3 times with DI water, filtered, and then dried at 80° C. The composition was 27.1% Fe and 72.9% Si by weight. The surface area of the sample was 320 m$^2$/g. The pore volume of the sample was 0.74 cm$^3$/g. Particle size was less than 40 mesh.

Example 11: Precipitated Iron Hydroxide

A precipitated iron hydroxide was prepared by dissolving 120 g NaOH in 1 liter DI water along with 20 g of Polycat-41 as a structure directing agent. 267 of iron chloride was dissolved in DI water to a final weight solution weight of 807 g. The entire solution was added over a 30 minute period using a peristaltic pump to the caustic solution and achieved a pH of 8.0. The resulting slurry was mixed for 4 hours, then allowed to stand overnight. In the morning, the gel was re-mixed, filtered, and then washed 3 times with DI water. The filtered product was dried overnight at 80° C. The surface area of the sample was 180 m$^2$/g. The pore volume of the sample was 0.15 cm$^3$/g. Particle size was less than 40 mesh.

Example 12: Precipitated Iron-Aluminum Hydroxide

An iron-aluminum hydroxide was prepared by dissolving 100 g of sodium hydroxide and 100 g of sodium aluminate in 1.5 L of DI water at 90° C. Once dissolved, 30 g of tetrapropylammonium bromide was added as a structure directing agent, and the solution was allowed to cool to room temperature under agitation. A second solution was prepared by dissolving 200 g of iron chloride in 500 g of DI water plus 50 grams of sulfuric acid. With both solutions at room temperature, the iron chloride solution was added to the sodium aluminate solution to a pH of 8. This required 640 g of the iron chloride solution. The resulting gel was mixed for three hours, then allowed to stand overnight. In the morning, the material was remixed for 5 minutes, and then filtered. The material was then washed three times with DI water, with the filtered solids dried overnight at 80° C. The resulting material was 44% aluminum and 56% iron by weight. The surface area of the sample was 355 m$^2$/g. The pore volume of the sample was 0.35 cm$^3$/g. Particle size was less than 40 mesh.

Example 13: Precipitated Iron-Silicon-Aluminum Hydroxide

A precipitated iron-silicon-aluminum hydroxide was prepared as follows. 80 g of sodium hydroxide, 20 g of sodium silicate solution (20% $SiO_2$), and 80 grams of sodium aluminate were added to 1.5 L of DI water. The slurry was heated to 65° C. in order to dissolve the sodium aluminate. Once dissolved, the solution was mixed and allowed to cool to room temperature. At this time, 30 g of tetrapropylammonium bromide was added to the solution. A second solution was prepared by dissolving 300 g of iron chloride in 800 grams of DI water. The iron chloride solution was added to the sodium aluminate-sodium silicate solution until a pH of 8 was achieved. This required 738 g of solution. The resulting slurry was mixed for 3.5 hours then allowed to stand overnight. In the morning, the slurry was remixed for 5 minutes, and then filtered. The material was then washed three times in DI water, then dried overnight at 80° C. The resulting material was 33% Al/4% Si/63% Fe by weight. The surface area of the sample was 303 $m^2/g$. The pore volume of the sample was 0.41 $cm^3/g$. Particle size was less than 40 mesh.

Example 14: Precipitated Magnesium-Iron-Silicon Hydroxide

A magnesium-iron-silicon hydroxide was prepared by adding 80 grams of sodium hydroxide and 100 grams of sodium silicate solution (28% $SiO_2$) to 1 L of DI water. Once blended, 30 grams of tetrapropylammonium bromide was added. A second solution was prepared by dissolving 200 grams of iron chloride and 100 grams of magnesium chloride in 550 grams of DI water. The iron-magnesium solution was added to the sodium aluminate solution to a pH of 8. This required 614 g of solution. The precipitated material was blended for 3.5 hours, then allowed to stand overnight. In the morning, the material was remixed for 5 minutes, and then filtered. The material was then washed three times in DI water, with the resulting solids dried overnight at 80° C. The resulting material was 16% Mgl/27% Si/57% Fe by weight. The surface area of the sample was 446 $m^2/g$. The pore volume of the sample was 0.38 $cm^3/g$. Particle size was less than 40 mesh.

Example 15: Precipitated Cobalt Hydroxide

A precipitated cobalt hydroxide was also prepared by dissolving 100 g of sodium hydroxide in 1.5 L of DI water. Once dissolved, 30 grams of tetrapropylammonium bromide was added as a structure directing agent. A second solution was prepared by dissolving 200 grams of cobalt nitrate in 500 g of DI water. The pH of the slurry was at 13 following the addition of the cobalt nitrate solution. 32 g of sulfuric acid was added to reduce the pH of the slurry to 8.0. The slurry was mixed for 3.5 hours during which the solution was maintained at pH 8 using sulfuric acid. The material was allowed to age overnight at room temperature. In the morning, the precipitated cobalt hydroxide was mixed for 5 minutes, and then filtered. The resulting solids were washed three times in DI water. Following the last washing, the solids were filtered and dried overnight at 80° C. The surface area of the sample was 43 $m^2/g$. The pore volume of the sample was 0.15 $cm^3/g$. Particle size was less than 40 mesh.

Example 16: Preparation of Cobalt-Zirconium Hydroxide

A precipitated cobalt-zirconium hydroxide was prepared by adding 1.5 liter of DI water to a 4 liter pail, along with 50 g of tetrapropyl ammonium bromide as a structure directing agent. The pH of the slurry was adjusted to 11 using KOH. A zirconium cobalt solution was prepared by dissolving 143.3 g of cobalt chloride (34.9 wt. % $Co_2O_3$) in 750 ml of zirconium oxychloride (20% $ZrO_2$). The cobalt zirconia solution was added using a peristaltic pump over a 30 minute period with the pH maintained at 11 using a 50% KOH solution as a buffer. Upon completion, the pH of the slurry was monitored and reduced back to 11 using $H_2SO_4$. Following 4 hours of mixing, the slurry was allowed to stand overnight. In the morning, the slurry was washed twice with 3 liters of DI water, then filtered and dried at 80° C. The surface area of the sample was 260 $m^2/g$. The pore volume of the sample was 0.26 $cm^3/g$. Particle size was less than 40 mesh.

Example 17: Preparation of Copper Hydroxide

Copper hydroxide was prepared by dissolving 100 g copper chloride (37.5% Cu) in 250 ml DI water. To the copper chloride solution was added 10 g of tetrapropylammonium bromide as a structure directing agent. A sodium hydroxide solution was prepared by dissolving 60 g NaOH in 150 ml DI water. The NaOH solution was added to the copper chloride solution to a pH of 8. The slurry was mixed for an additional 4 hours, then allowed to stand overnight. In the morning, the resulting copper hydroxide was filtered from the solution, then washed three times using DI water. Following washing, the material was dried at 80° C. overnight. The surface area of the sample was 130 $m^2/g$. The pore volume of the sample was 0.37 $cm^3/g$. Particle size was less than 40 mesh.

Example 18: Preparation of Calcium Hydroxide

Calcium hydroxide was prepared by dissolving 350 g calcium nitrate in one liter DI water. 25 g of polyethylene glycol (average molecular weight=1,450) was added as a structure directing agent. A sodium carbonate/sodium hydroxide solution was prepared by adding 31 g of sodium carbonate and 60 g sodium hydroxide to 500 ml DI water in a Teflon beaker. The sodium carbonate/sodium hydroxide solution was then added to the calcium hydroxide solution while mixing. The pH of the calcium hydroxide solution was about 8, but rapidly increases to greater than 11 upon the addition of just a few drops of sodium hydroxide/sodium carbonate solution. The final pH of the solution was 12.4. A white precipitate formed upon addition of each drop of basic solution. The slurry was mixed for 30 minutes, then aged overnight at room temperature. In the morning, the solution was mixed, then filtered and washed 3 times with DI water. The product was dried at 80° C. overnight in a forced convection oven. The surface area of the sample was 29 $m^2/g$. The pore volume of the sample was 0.15 $cm^3/g$. Particle size was less than 40 mesh.

Example 19: Preparation of Zirconium Hydroxide

A precipitated zirconium hydroxide was prepared by adding 1.5 liter of DI water to a 4 liter pail, along with 50 g of tetrapropyl ammonium bromide as a structure directing agent. The pH of the slurry was adjusted to 11 using KOH. 750 ml of zirconium oxychloride (20% $ZrO_2$) was added using a peristaltic pump over a 30 minute period with the pH maintained at 11 using a 50% KOH solution as a buffer. Upon completion, the pH of the slurry was monitored and reduced back to 11 using $H_2SO_4$. Following 4 hours of mixing, the slurry was allowed to stand overnight. In the morning, the slurry was washed twice with 3 liters of DI water, then filtered and dried at 80° C. The surface area of the sample was 275 m²/g. The pore volume of the sample was 0.41 cm³/g. Particle size was less than 40 mesh.

Example 20: Preparation of 7% KMnO₄ Impregnated Zirconium Hydroxide

To 75 ml of DI water was added 7.0 g of potassium permanganate (KMnO₄). The solution was stirred at room temperature until all the KMnO₄ was dissolved. Zirconium hydroxide powder prepared as in Example 16 was dried at 80° C. overnight to a moisture loading of less than 3% water. 100 g of the dried zirconium hydroxide was impregnated by adding dropwise the KMnO₄ solution while blending the solids. Upon completion of the impregnation operation, the resulting solids were placed in a forced convection oven and dried overnight at 80° C. In the morning, the 7% KMnO₄/Zr(OH)₄ was removed from the oven and placed in a sealed container.

Example 21: Preparation of 5% CuCl₂ Impregnated Zirconium Hydroxide

To 75 ml of DI water was added 6.35 g of copper (II) chloride dihydrate (CuCl₂.2H₂O—78.9% CuCl₂ by weight). The solution was stirred at room temperature until all the CuCl₂.2H₂O was dissolved. Zirconium hydroxide powder as prepared in Example 16 was dried at 80° C. overnight to a moisture loading of less than 3% water. 100 g of the dried zirconium hydroxide was impregnated by adding dropwise the CuCl₂.2H₂O solution while blending the solids. Upon completion of the impregnation operation, the resulting solids were placed in a forced convection oven and dried overnight at 80° C. In the morning, the 5% CuCl₂/Zr(OH)₄ was removed from the oven and placed in a sealed container.

Example 22: Preparation of 5% Co(OH)₂ Loaded Zirconium Hydroxide

To a 1 gallon vessel was added 1.5 liters DI water plus 300 g zirconium hydroxide (dry basis) prepared as in Example 16. The pH of the zirconium hydroxide in the vessel was adjusted to pH=11 using a potassium hydroxide solution. A cobalt sulfate solution was prepared by dissolving 42.5 g of cobalt sulfate hexahydrate (CoSO₄.6H₂O—35.3% Co(OH)₂ by weight) in 500 ml DI water. The cobalt sulfate solution was added to the zirconium hydroxide slurry at a rate of 15 ml/min using a peristaltic pump. During precipitation, the pH of the slurry was maintained at 11.0 using a 35% KOH solution. Upon completion of the addition, the slurry was allowed to mix for 4 hours, then stand overnight. In the morning, the slurry was re-mixed and filtered, then washed with DI water to remove the residual potassium. Once washed, the resulting 5% Co(OH)₂/Zr(OH)₄ powder was placed in a forced convection oven and dried overnight at 80° C. In the morning, the powder was removed from the oven and placed in a sealed container.

Example 23: Preparation of Cu(NO₃)₂ Loaded Aluminum Silicate

A precipitated silicon-aluminum hydroxide was prepared as follows. 2 g of sodium hydroxide, 0.6 g of sodium silicate solution (30% SiO₂), and 2 g of sodium aluminate were added to 1 mL of methanol. The slurry was gently heated to 70° C. in order to dissolve the sodium aluminate. Once dissolved, the solution was mixed and allowed to cool to room temperature. A solution was prepared by dissolving 2 g of copper (II) nitrate in 0.2 mL of methanol. The copper (II) nitrate solution was added to the sodium aluminate-sodium silicate solution and resulted with a pH of 8. The resulting slurry was mixed for 3 hours then allowed to stand overnight. The next day the slurry was remixed for 5 minutes, and then filtered. The material was then washed three times in methanol, then dried overnight at 80° C. The surface area of the sample was 2120 m²/g. The pore volume of the sample was 0.34 cm³/g.

Example 24: Preparation of Ni(NO₃)₂ Loaded Aluminum Silicate

A precipitated silicon-aluminum hydroxide was prepared as follows. 2 g of sodium hydroxide, 0.6 g of sodium silicate solution (30% SiO₂), and 2 g of sodium aluminate were added to 1 mL of methanol. The slurry was gently heated to 70° C. in order to dissolve the sodium aluminate. Once dissolved, the solution was mixed and allowed to cool to room temperature. A solution was prepared by dissolving 2 g of nickel (II) nitrate in 0.2 mL of methanol. The nickel (II) nitrate solution was added to the sodium aluminate-sodium silicate solution and resulted with a pH of 8. The resulting slurry was mixed for 3 hours then allowed to stand overnight. The next day the slurry was remixed for 5 minutes, and then filtered. The material was then washed three times in methanol, then dried overnight at 80° C.

Example 25: Preparation of Co(NO₃)₂ Loaded Aluminum Silicate

A precipitated silicon-aluminum hydroxide was prepared as follows. 2 g of sodium hydroxide, 0.6 g of sodium silicate solution (30% SiO₂), and 2 g of sodium aluminate were added to 1 mL of methanol. The slurry was gently heated to 70° C. in order to dissolve the sodium aluminate. Once dissolved, the solution was mixed and allowed to cool to room temperature. A solution was prepared by dissolving 2 g of cobalt (II) nitrate in 0.2 mL of methanol. The cobalt (II) nitrate solution was added to the sodium aluminate-sodium silicate solution and resulted with a pH of 8. The resulting slurry was mixed for 3 hours then allowed to stand overnight. The next day the slurry was remixed for 5 minutes, and then filtered. The material was then washed three times in methanol, then dried overnight at 80° C.

Example 26: Preparation of Fe(NO₃)₃ Loaded Aluminum Silicate

A precipitated silicon-aluminum hydroxide was prepared as follows. 2 g of sodium hydroxide, 0.6 g of sodium silicate solution (30% SiO₂), and 2 g of sodium aluminate were added to 1 mL of methanol. The slurry was gently heated to 70° C. in order to dissolve the sodium aluminate. Once dissolved, the solution was mixed and allowed to cool to room temperature. A solution was prepared by dissolving 2 g of iron (III) nitrate in 0.2 mL of methanol. Other valent states of iron could be used as well. The iron (III) nitrate solution was added to the sodium aluminate-sodium silicate solution and resulted with a pH of 8. The resulting slurry was mixed for 3 hours then allowed to stand overnight. The next day the slurry was remixed for 5 minutes, and then filtered. The material was then washed three times in methanol, then dried overnight at 80° C.

Example 27: Preparation of M-Aluminum Silicate (M=$Cu^{2+}$, $Ni^{2+}$, $Co^{2+}$, $Fe^{3+}$)

A precipitated M-aluminum silicates was prepared as follows. 6 g of sodium silicate solution and 0.2 g of sodium aluminate were added to 2 mL of methanol. The slurry was gently heated to 70° C. in order to dissolve the sodium aluminate. Once dissolved, the solution was mixed and allowed to cool to room temperature. A solution was prepared by dissolving at least 6 g of M-nitrate (M=$Cu^{2+}$, $Ni^{2+}$, $Co^{2+}$, $Fe^{3+}$) in 1 mL of methanol. Other valent states of the cations could be used as well. The M-nitrate solution was added to the solution. The resulting slurry was mixed for 5 hours then allowed to stand overnight. The product was vacuum-filtered followed by washing 3 times with methanol, and then dried overnight at 110° C.

Example 28: Preparation of M-Aluminum Titanium Silicate (M=$Cu^{2+}$, $Ni^{2+}$, $Co^{2+}$, $Fe^{3+}$)

A precipitated M-silicon aluminum titanium hydroxide was prepared as follows. 6 g of sodium silicate solution, 0.2 g of sodium aluminate, and 3 g of titanium (IV) oxide were added to 2 mL of methanol. The slurry was gently heated to 70° C. in order to dissolve the sodium aluminate. Once dissolved, the solution was mixed and allowed to cool to room temperature. A solution was prepared by dissolving at least 6 g of M-nitrate (M=$Cu^{2+}$, $Ni^{2+}$, $Co^{2+}$, $Fe^{3+}$) in 1 mL of methanol. Other valent states of the cations could be used as well. The M-nitrate solution was added to the solution. The resulting slurry was mixed for 5 hours then allowed to stand overnight. The product was vacuum-filtered followed by washing 3 times with methanol, and then dried overnight at 110° C.

Example 29: Preparation of M-Aluminum Titanium Phosphorus Silicate (M=$Cu^{2+}$, $Ni^{2+}$, $Co^{2+}$, $Fe^{3+}$)

A precipitated M-silicon aluminum titanium phosphorus hydroxide was prepared as follows. 6 g of sodium silicate solution, 0.2 g of sodium aluminate, 3 g of titanium (IV) oxide, and 0.2 g of phosphoric acid were added to 3 mL of methanol. The slurry was gently heated to 70° C. in order to dissolve the sodium aluminate. Once dissolved, the solution was mixed and allowed to cool to room temperature. A solution was prepared by dissolving at least 6 g of M-nitrate (M=$Cu^{2+}$, $Ni^{2+}$, $Co^{2+}$, $Fe^{3+}$) in 1 mL of methanol. Other valent states of the cations could be used as well. The M-nitrate solution was added to the solution. The resulting slurry was mixed for 5 hours then allowed to stand overnight. The product was vacuum-filtered followed by washing 3 times with methanol, and then dried overnight at 110° C.

Example 30: Preparation of Films Using M-Aluminum Silicate (M=$Cu^{2+}$, $Ni^{2+}$, $Co^{2+}$, $Fe^{3+}$)

Using the described M-aluminum silicate mixtures above, different films were prepared in various ratios (1:1, 2:1, 3:1, 4:1) of the material of interest with a polymer. The polymers used were poly(methyl)methacrylate (PMMA), poly(tetrafluoroethylene) (Teflon), polyethylene terephthalate, poly (styrene-co-butadiene). The mixtures were stirred for 1 h with 1 mL of methanol followed by gently heating to 50° C. overnight. Once the powders were dry, 1 mL of tetrahydrofuran solution was added to the powder in a petri dish. The solution was set aside to dry overnight.

Example 31: Preparation of Films Using M-Aluminum Silicate (M=$Cu^{2+}$, $Ni^{2+}$, $Co^{2+}$, $Fe^{3+}$)

Using the described M-aluminum silicate mixtures above, different films were prepared in various ratios (1:1, 2:1, 3:1, 4:1) of the material of interest with a polymer. The polymers used were poly(methyl)methacrylate (PMMA), poly(tetrafluoroethylene) (Teflon), polyvinylidene fluoride, polyethylene terephthalate, and poly(styrene-co-butadiene). The mixtures were stirred for 1 h with 1 mL of methanol followed by gently heating to 50° C. overnight. Once the powders were dry, 1 mL of tetrahydrofuran solution was added to the powder in a petri dish. The solution was set aside to dry overnight.

Example 32 Preparation of Films Using M-Aluminum Titanium Silicate (M=$Cu^{2+}$, $Ni^{2+}$, $Co^{2+}$, $Fe^{3+}$)

Using the described M-aluminum titanium silicate mixtures above, different films were prepared in various ratios (1:1, 2:1, 3:1, 4:1) of the material of interest with a polymer. The polymers used were poly(methyl)methacrylate (PMMA), poly(tetrafluoroethylene) (Teflon), polyvinylidene fluoride, polyethylene terephthalate, and poly(styrene-co-butadiene). The mixtures were stirred for 1 h with 1 mL of methanol followed by gently heating to 50° C. overnight. Once the powders were dry, 1 mL of tetrahydrofuran solution was added to the powder in a petri dish. The solution was set aside to dry overnight.

Example 33: Preparation of Films Using M-Aluminum Titanium Phosphorus Silicate (M=$Cu^{2+}$, $Ni^{2+}$, $Co^{2+}$, $Fe^{3+}$)

Using the described M-aluminum titanium phosphorus silicate mixtures above, different films were prepared in various ratios (1:1, 2:1, 3:1, 4:1) of the material of interest with a polymer. The polymers used were poly(methyl) methacrylate (PMMA), poly(tetrafluoroethylene) (Teflon), polyvinylidene fluoride, polyethylene terephthalate, and poly(styrene-co-butadiene). The mixtures were stirred for 1 h with 1 mL of methanol followed by gently heating to 50° C. overnight. Once the powders were dry, 1 mL of tetrahydrofuran solution was added to the powder in a petri dish. The solution was set aside to dry overnight.

Example 34: Visual Detection of the Presence of Toxic Chemicals

The 7% $KMnO_4$/$Zr(OH)_4$ of Example 20, the 5% $CuCl_2$/$Zr(OH)_4$ of Example 21, and the 5% $Co(OH)_2$/$Zr(OH)_4$ of Example 22, each in powder form are used for the detection of the toxic chemicals $NH_3$, CK, $SO_2$, $H_2S$, and Octane using a microbreakthrough system essentially as described in Peterson, et al., *Ind. Eng. Chem. Res.* 2014; 53:701-707. Briefly, Microbreakthrough testing was conducted on a push system designed for evaluating small (~20 mg) quantities of powders substantially as described in Glover, et al., *Chem. Eng. Sci.,* 2011; 66 (2): 163-170. The test conditions included a temperature of 20° C., a relative humidity of 0% or 80%, the adsorbent mass was 10-60 mg, the adsorbent volume was 55 $mm^3$, the flow rate was 20 mL/min, and the concentrations of the toxic chemicals were as follows:

$NH_3$—2000 mg/m$^3$; octane—4000 mg/m$^3$; CK—4000 mg/m$^3$; $SO_2$—1000 mg/m$^3$; and $H_2S$—1000 mg/m$^3$. Sorbents were activated at 60° C. for 1 h in flowing dry air, equilibrated at the proper relative humidity (RH) for 2 h as applicable and then packed at a constant volume of approximately 50-55 mm$^3$ in a 4-mm-i.d. (nominal) fritted glass tube to a height of 4 mm. Each chemical was injected into a ballast and then pressurized. From the ballast the chemical was delivered to either a dry or humidified air stream at a rate necessary to achieve the desired challenge concentration. Water vapor was delivered to the system through a saturator cell within a water bath. The challenge was dosed to a packed bed until saturation (effluent=feed), after which the materials were purged with air to evaluate desorption. Effluent concentrations were monitored using Hewlett-Packard (HP) 5890 gas chromatographs equipped with a flame ionization detector and a photoionization detector for use with the various toxic chemicals. Microbreakthrough graphs are plotted on a mass-weighted basis to account for differences in density. Loadings were calculated in moles per kilogram by integrating the breakthrough curves to saturation. The standard system error is approximately 10%. The loadings of the various toxic chemicals are presented in Table 1.

TABLE 1

Chemical loadings (mol/kg) of metal-loaded $Zr(OH)_4$ samples with dry loading at an RH of 0% and wet loading at an RH of 80%.

| Sample | Ammonia | | Octane | | CK | | $SO_2$ | | $H_2S$ | |
| --- | --- | --- | --- | --- | --- | --- | --- | --- | --- | --- |
| | Dry | Wet | Dry | Wet | Dry | Wet | Dry | Wet | Dry | Wet |
| $Zr(OH)_4$ | 1.41 | 0.71 | 0.45 | 0.07 | 0.08 | 0.48 | 2.01 | 0.94 | 0.02 | 0.03 |
| +$Co(OH)_2$ | 1.55 | 0.67 | 0.24 | 0.04 | 0.04 | 0.09 | 2.12 | 1.02 | 0.44 | 0.22 |
| +$CuCl_2$ | 2.10 | 1.82 | 0.52 | 0.08 | 0.58 | 0.03 | 1.35 | 0.87 | 0.61 | 0.59 |
| +$KMnO_4$ | 1.00 | 0.70 | 0.62 | 0.07 | 0.07 | 0.05 | 3.99 | >12 | 1.00 | 2.07 |

The resulting color change was observed visually and as depicted in FIG. 1. Significant color changes are visually observed for each of the toxic chemicals relative to the water control. The most dramatic color changes were observed using 7% $KMnO_4/Zr(OH)_4$ and detection of toxic chemicals $SO_2$ and $H_2S$.

Example 35: Detection of the Presence of Toxic Chemicals by Spectroscopy

The 7% $KMnO_4/Zr(OH)_4$ of Example 20, the 5% $CuCl_2/Zr(OH)_4$ of Example 21, and the 5% $Co(OH)2/Zr(OH)_4$ of Example 22, each in powder form, are used for the detection of the toxic chemicals $NH_3$, $SO_2$, $H_2S$, octane, methyl bromide, and CNCl using the process of Example 34, but spectral status is detected by Attenuated total reflectance Fourier transform infrared (ATR-FTiR) spectroscopy. Briefly, data were collected on the sorbent materials either before exposure or following exposure to a toxic chemical using a Bruker Tensor 27 FTIR spectrometer with a platinum accessory and a single-reflection diamond crystal. Sixteen scans from 4000 to 600 cm$^{-1}$ were averaged, and the background was subtracted with a resolution of 4 cm$^{-1}$.

Figure 2:
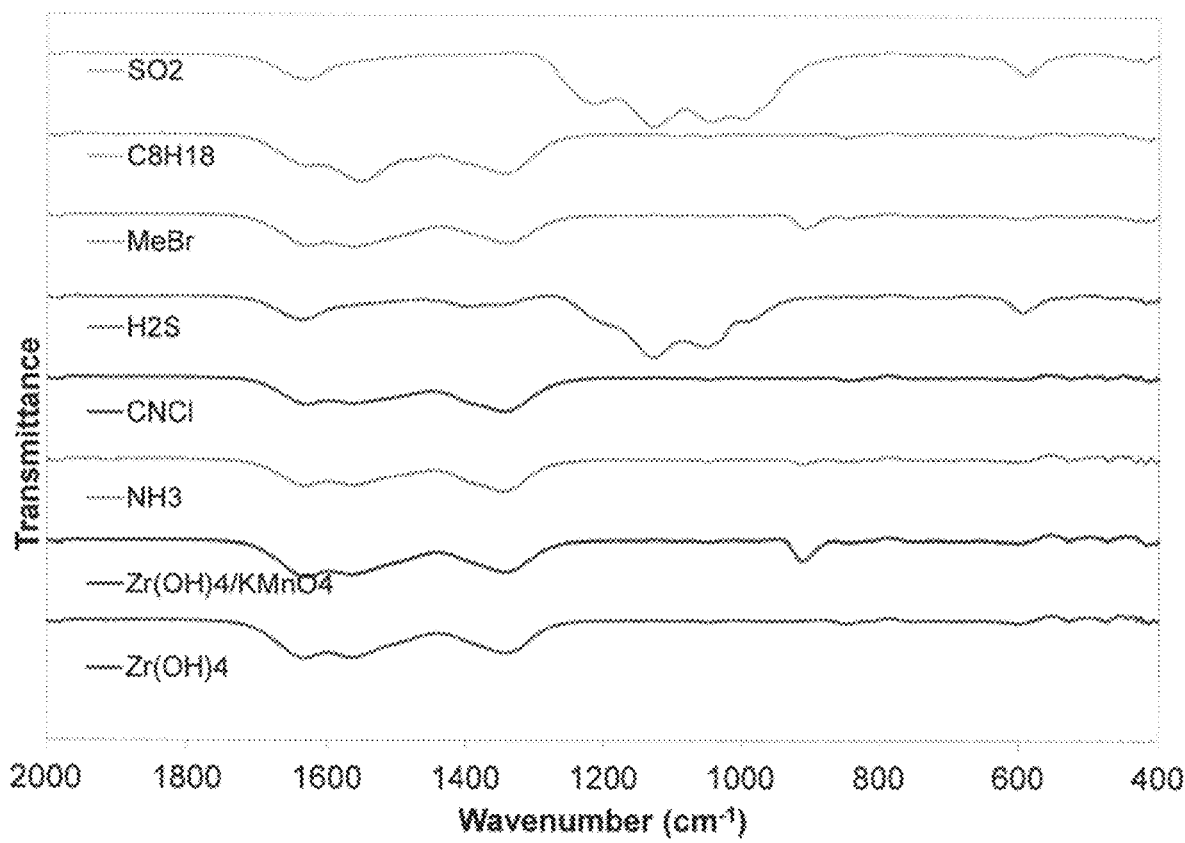
FIG. 2 illustrates FTIR analyses of colorimetric changes of the sorbent 7% $KMnO_4/Zr(OH)_4$ following exposure to an array of toxic chemicals.

The results of the 7% $KMnO_4/Zr(OH)_4$ material are depicted in FIG. 2. $NH_3$, CNCl, and to a lesser degree MeBr were detectable by a change in the peak near 900 cm$^{-1}$. Significant changes in the spectra were observed for $SO_2$, $H_2S$, and to a lesser degree octane. In sum, each of the toxic chemicals were detectable by changes in the spectrum as measured by FTIR.

Figure 3:
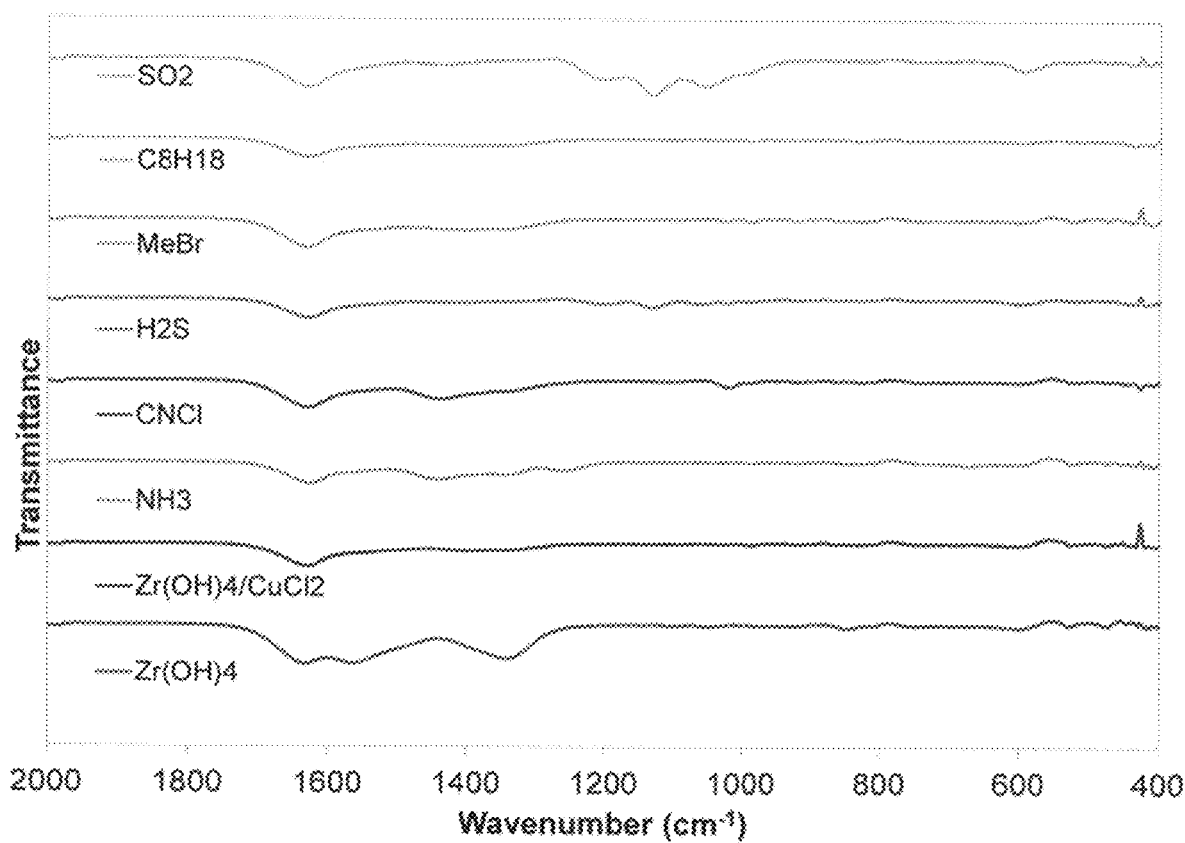
FIG. 3 illustrates FTIR analyses of colorimetric changes of the sorbent 5% $CuCl_2/Zr(OH)_4$ following exposure to an array of toxic chemicals.

The results of the 5% $CuCl_2/Zr(OH)_4$ material are depicted in FIG. 3. $SO_2$ showed the most dramatic change in spectra. $H_2S$ was detectably by spectral changes in the region of 1200 to 1000 cm$^{-1}$. CNCl caused a reduction in transmittance at approx. 1050 cm$^{-1}$. The remaining agents showed more modest alterations.

Figure 4:
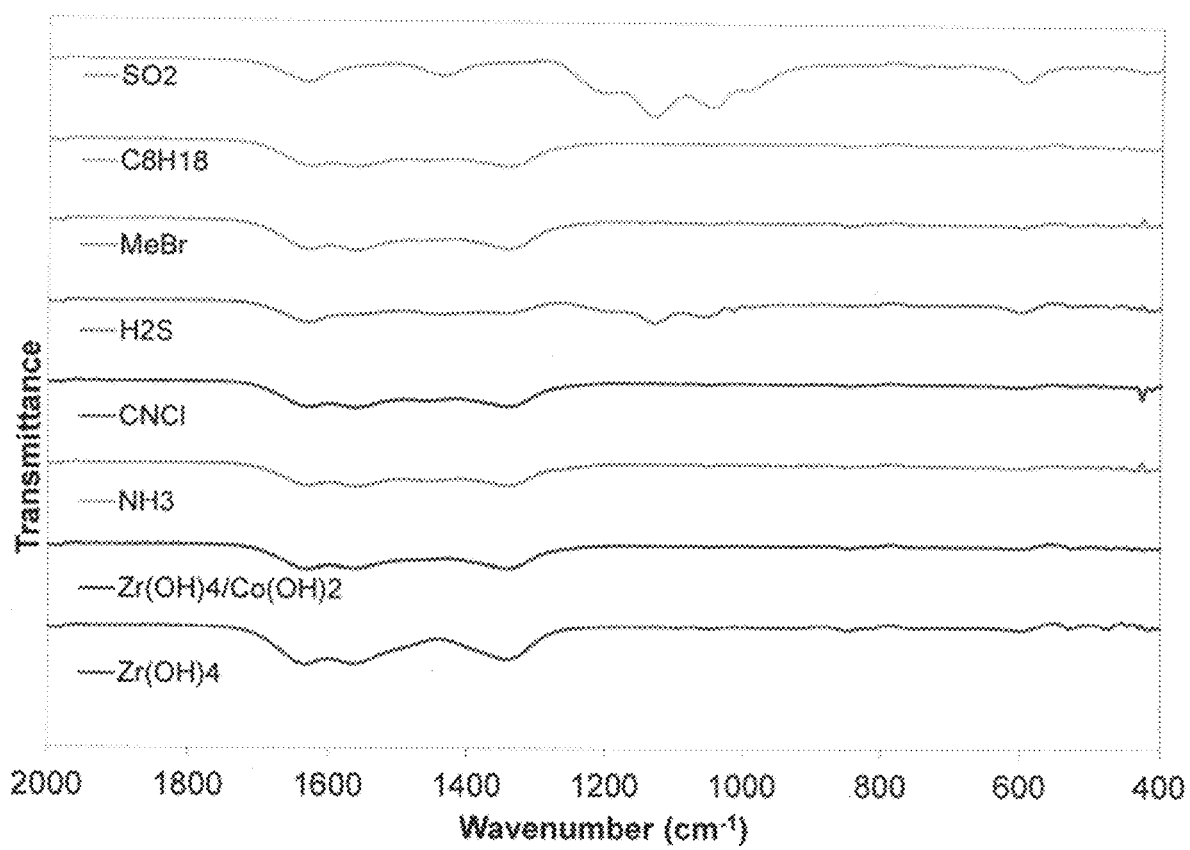
FIG. 4 illustrates FTIR analyses of colorimetric changes of the sorbent 5% $Co(OH)_2/Zr(OH)_4$ following exposure to an array of toxic chemicals.

The results of the 5% $Co(OH)_2/Zr(OH)_4$ material are depicted in FIG. 4. $SO_2$ showed the most dramatic change in spectra. $H_2S$ was detectably by spectral changes in the region of 1200 to 1000 cm$^{-1}$. The remaining agents showed more modest alterations.

Figure 5A:
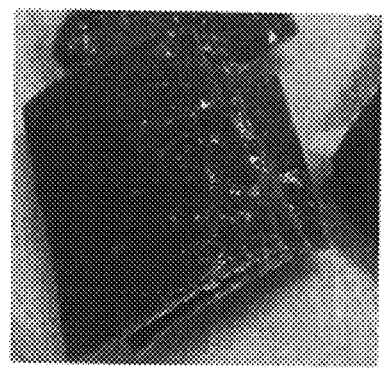
FIG. 5A illustrates the color of the sorbent $Zr(OH)_4$ impregnated with cobalt acetate, copper bromide, and copper sulfate impregnated into a polymer as synthesized prior to exposure to a toxic chemical.
Figure 5B:
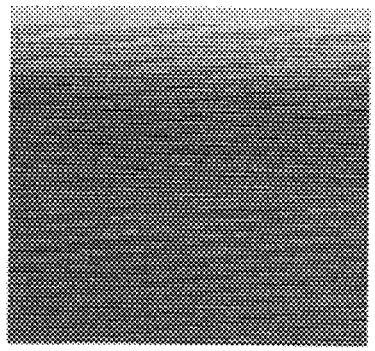
FIG. 5B illustrates the color change of the sorbent $Zr(OH)_4$ impregnated with cobalt acetate, copper bromide, and copper sulfate impregnated into a polymer following exposure to the toxic chemical H2S.
Figure 5C:
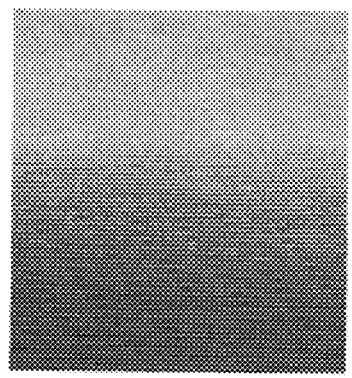
FIG. 5C illustrates the color change of the sorbent $Zr(OH)_4$ impregnated with cobalt acetate, copper bromide, and copper sulfate impregnated into a polymer following exposure to the toxic chemical hydrogen cyanide.

Example 36: Detection of $H_2S$ any Hydrogen Cyanide Using Sorbents Embedded on Polymer Results are depicted in FIG. 5. Zirconium hydroxide made with cobalt acetate, copper bromide, and copper sulfate were mixed together, forming a bluish-purple powder. The powder was mixed with a polymer, and then applied to a substrate, in this case filter paper. The polymer was allowed to thicken and harden overnight, after which the material was dosed with concentrated hydrogen sulfide and concentration hydrogen cyanide. It is appreciated that all reagents are obtainable by sources known in the art unless otherwise specified.

Example 37: Detection of the Presence of Toxic Chemicals by Spectroscopy

The M-aluminum silicates of Example D, the M-aluminum titanium silicates of Example E, and the M-aluminum titanium phosphorus silicates of Example F, each in powder form, are used for the detection of the toxic chemicals, e.g. G-type, V-type, and H-type chemical agents as well as opioids. The spectral status is detected by ultra-violet visual (UV-Vis) spectroscopy. Briefly, data were collected on the sorbent materials either before exposure or following exposure to a toxic chemical using a JASCO V-750 spectrophotometer with an integrating solid state sample holder. Scans were collected from 200 to 800 nm, and the background was subtracted.

Figure 6:
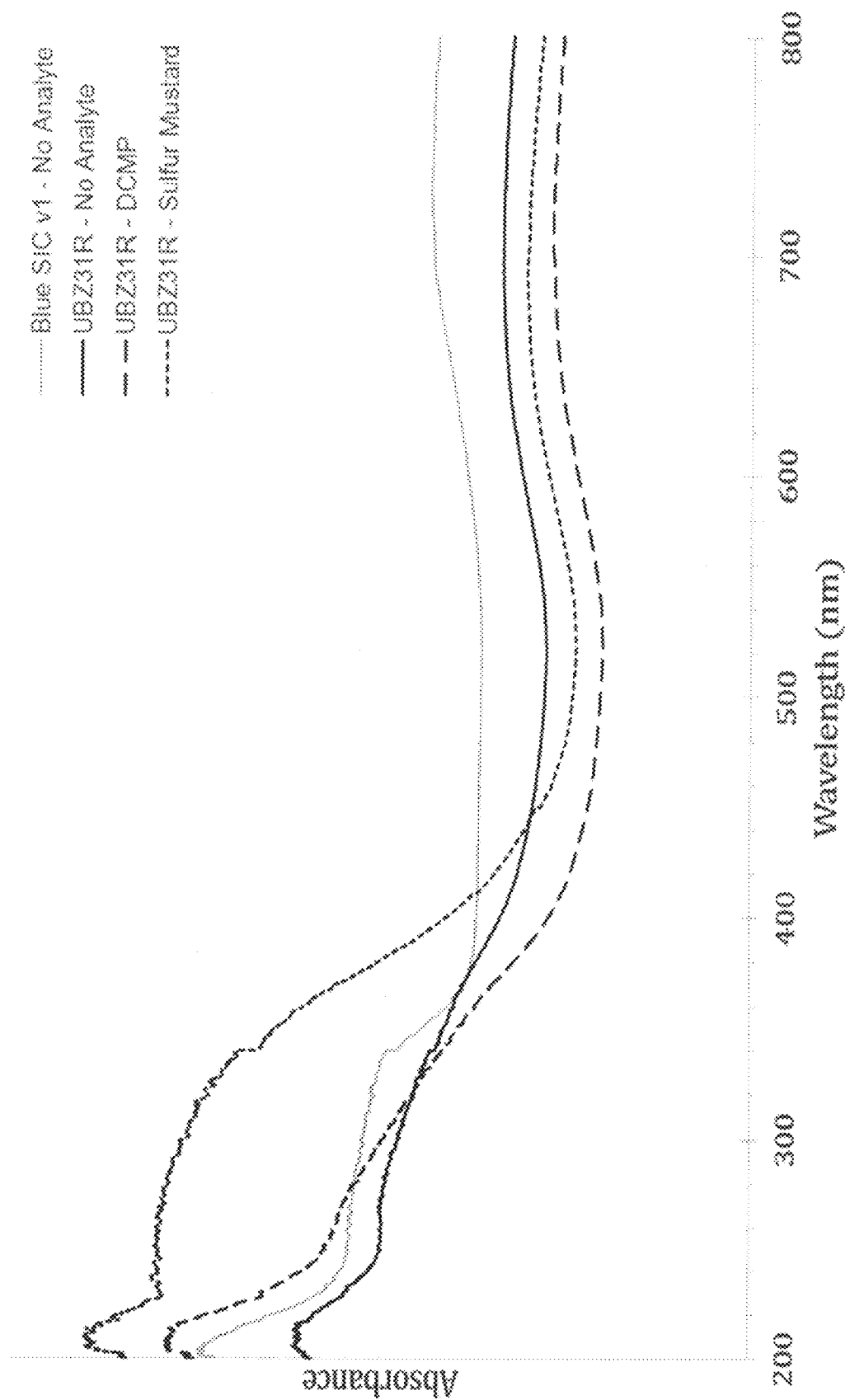
FIG. 6 illustrates the UV-Visible spectra showing unexposed blue self-indicating colorimetric response material version 1 (solid grey line) and unexposed UBZ31R self-indicating colorimetric response metal oxyhydroxide material (solid black line). The UBZ31R was exposed to dichloromethyl phosphonate (long dashed black line) and sulfur mustard (dotted black line). The spectra shows a change in color from blue to yellow-green color upon chemical exposure.

The results of Blue self-indicating colorimetric (SIC) v1 response material and copper aluminum silicate material (UBZ31R) are depicted in FIG. 6. Significant changes in the UV-Vis spectra were observed for dimethyl chlorophosphate (DMCP) and sulfur mustard. In summary, each of the toxic chemicals were detectable by changes in the spectrum as measured by UV-Vis.

Figure 7:
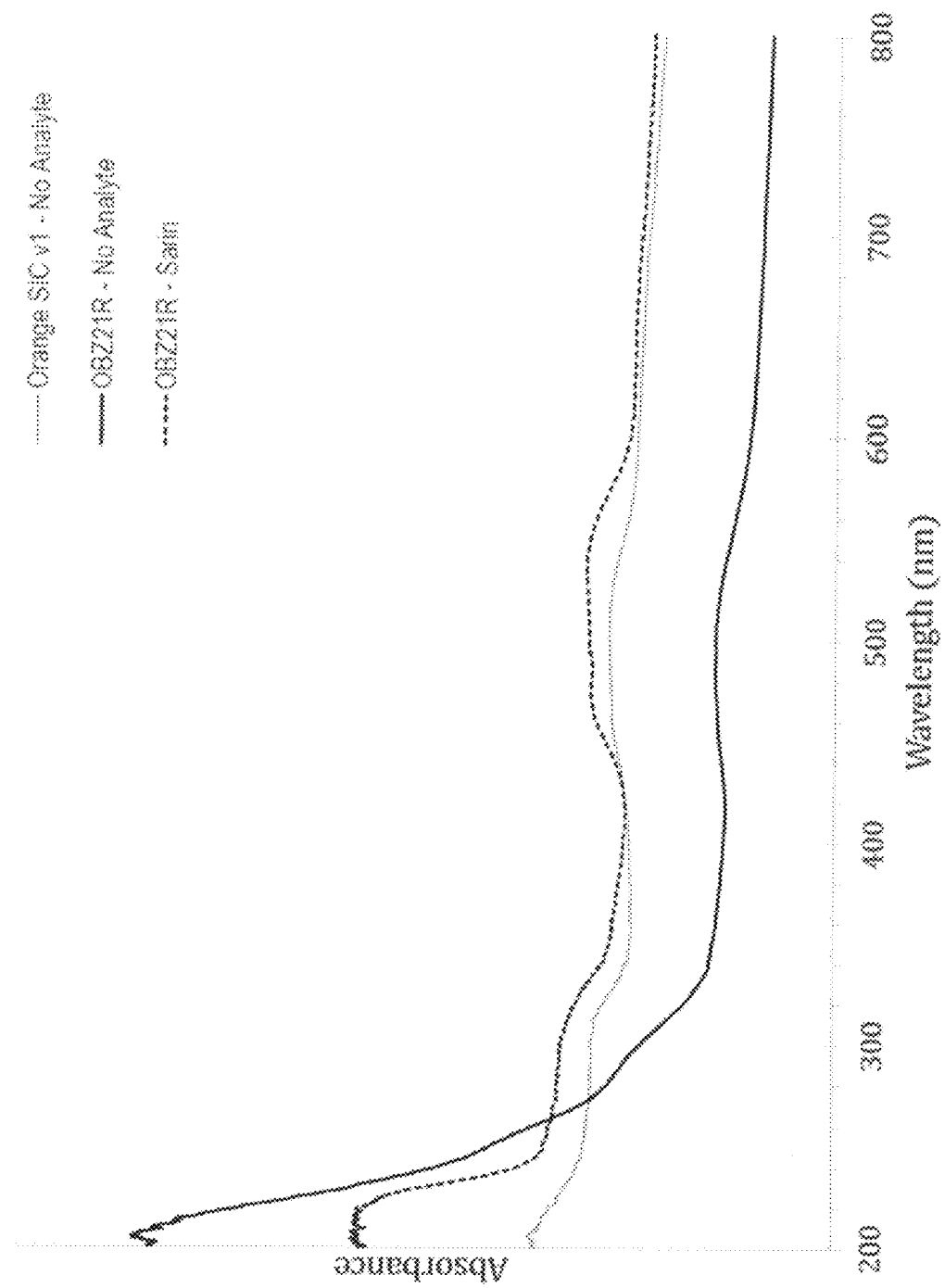
FIG. 7 illustrates UV-Visible spectra showing unexposed orange self-indicating colorimetric response material version 1 (solid grey line) and OBZ21R self-indicating colorimetric response material (solid black line). The black dotted line is OBZ21R material exposed to sarin. The latter spectra shows a change in color from pink to purple color upon chemical exposure.
Figure 8:
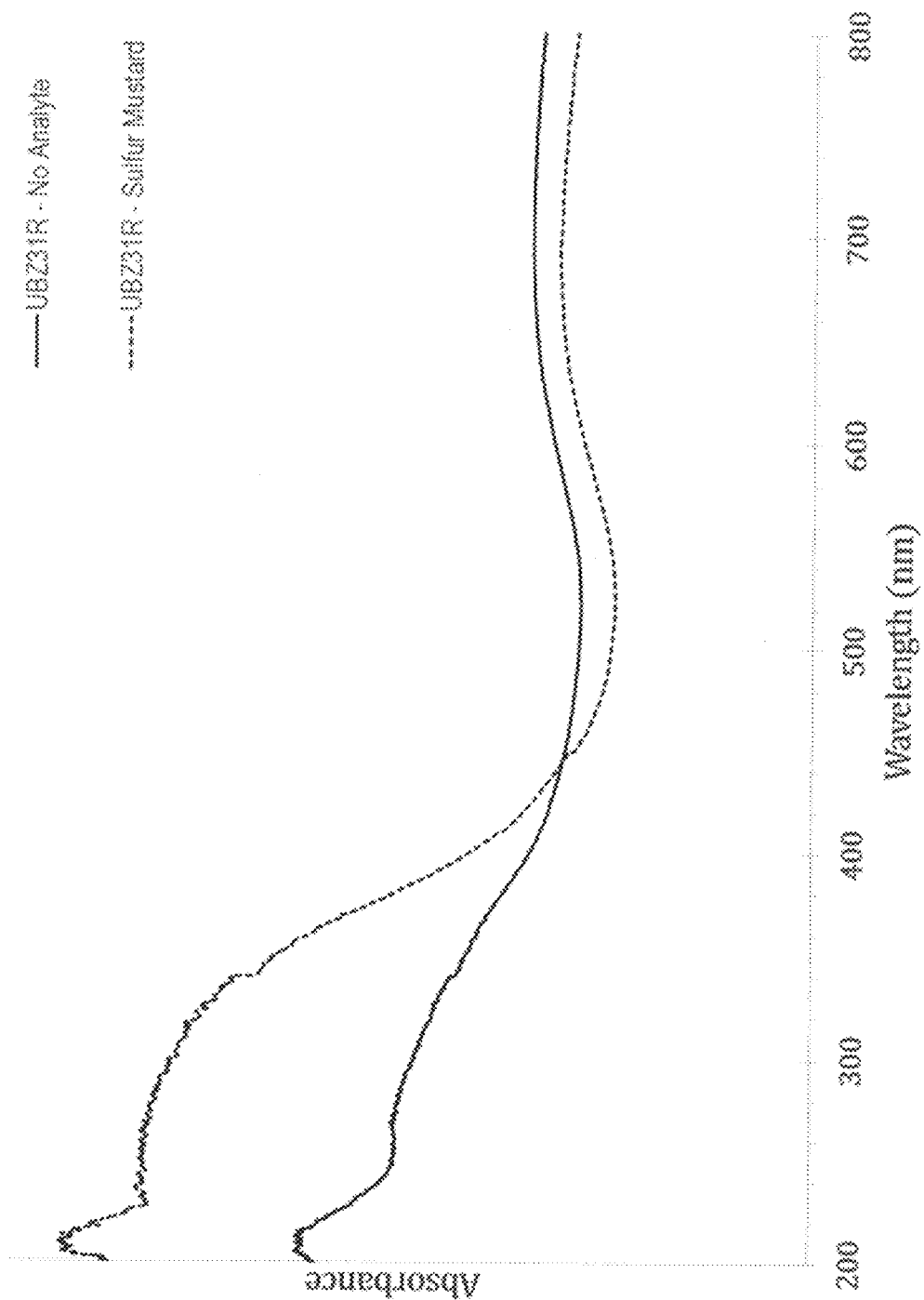
FIG. 8 illustrates UV-Visible spectra showing unexposed UBZ31R self-indicating colorimetric response material (solid black line) exposed to sulfur mustard (dotted black line). The spectra shows a change in color from blue to yellow-green color upon chemical exposure.
Figure 9:
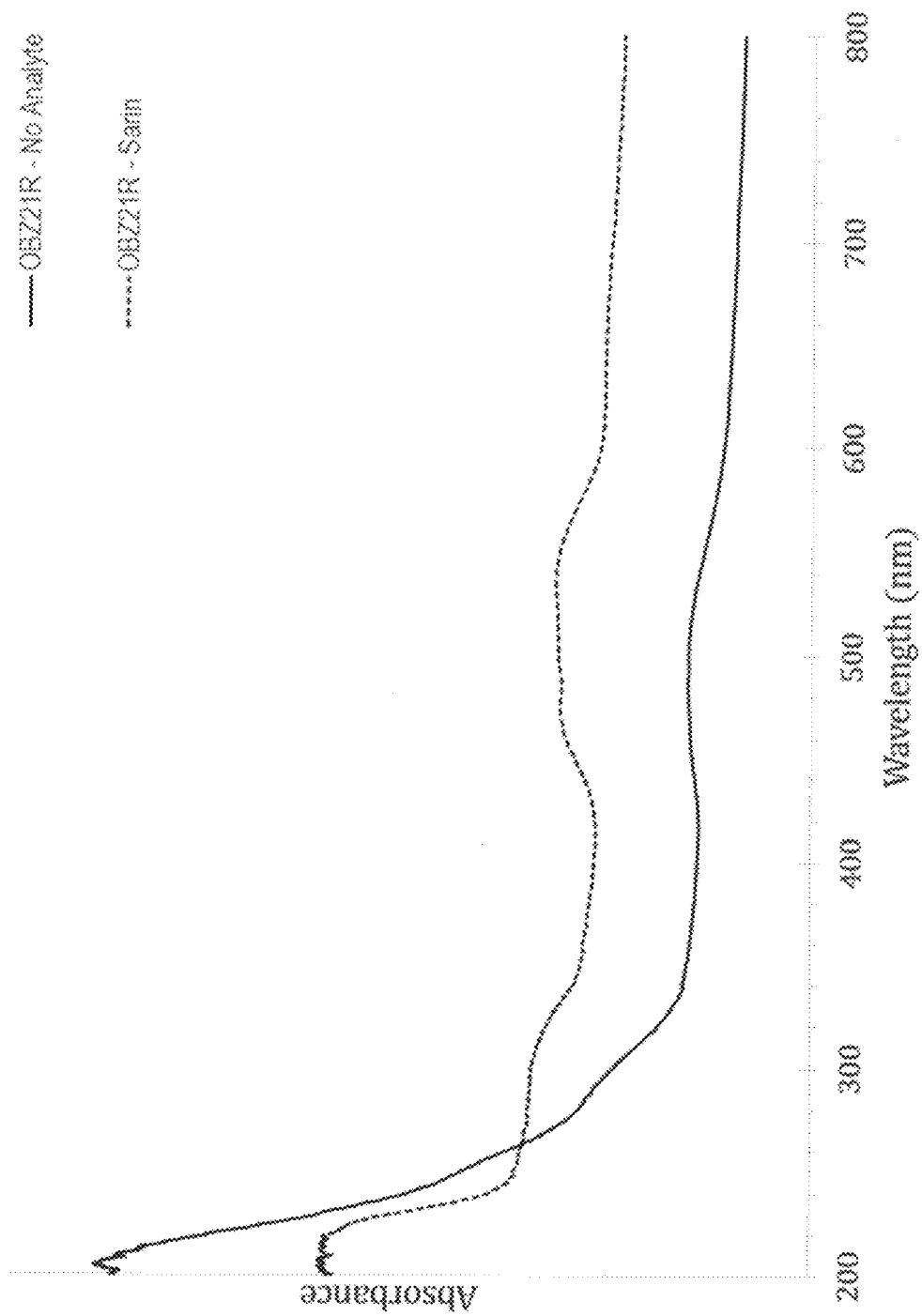
FIG. 9 illustrates UV-Visible spectra showing unexposed OBZ21R self-indicating colorimetric response material (solid black line) exposed to satin (dotted black line). The spectra shows a change in color from pink to purple color upon chemical exposure.
Figure 10:
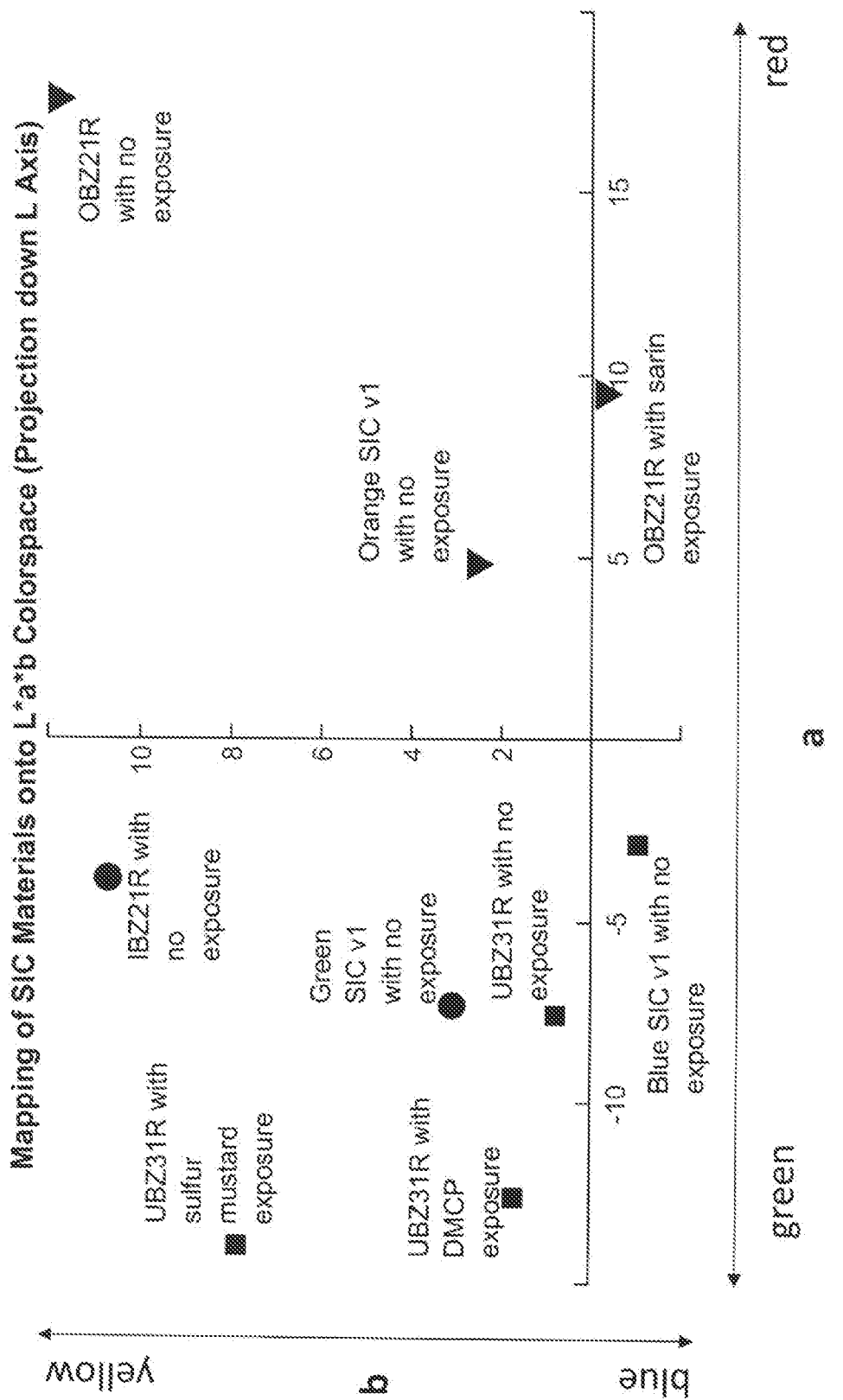
FIG. 10 shows mapping onto a L*a*b color space plot of self-indicating colorimetric (SIC) response materials exposed to various analytes. The projection view is down the L axis (light to dark in color). The plot shows the changes in color upon chemical exposure.
Figure 11:
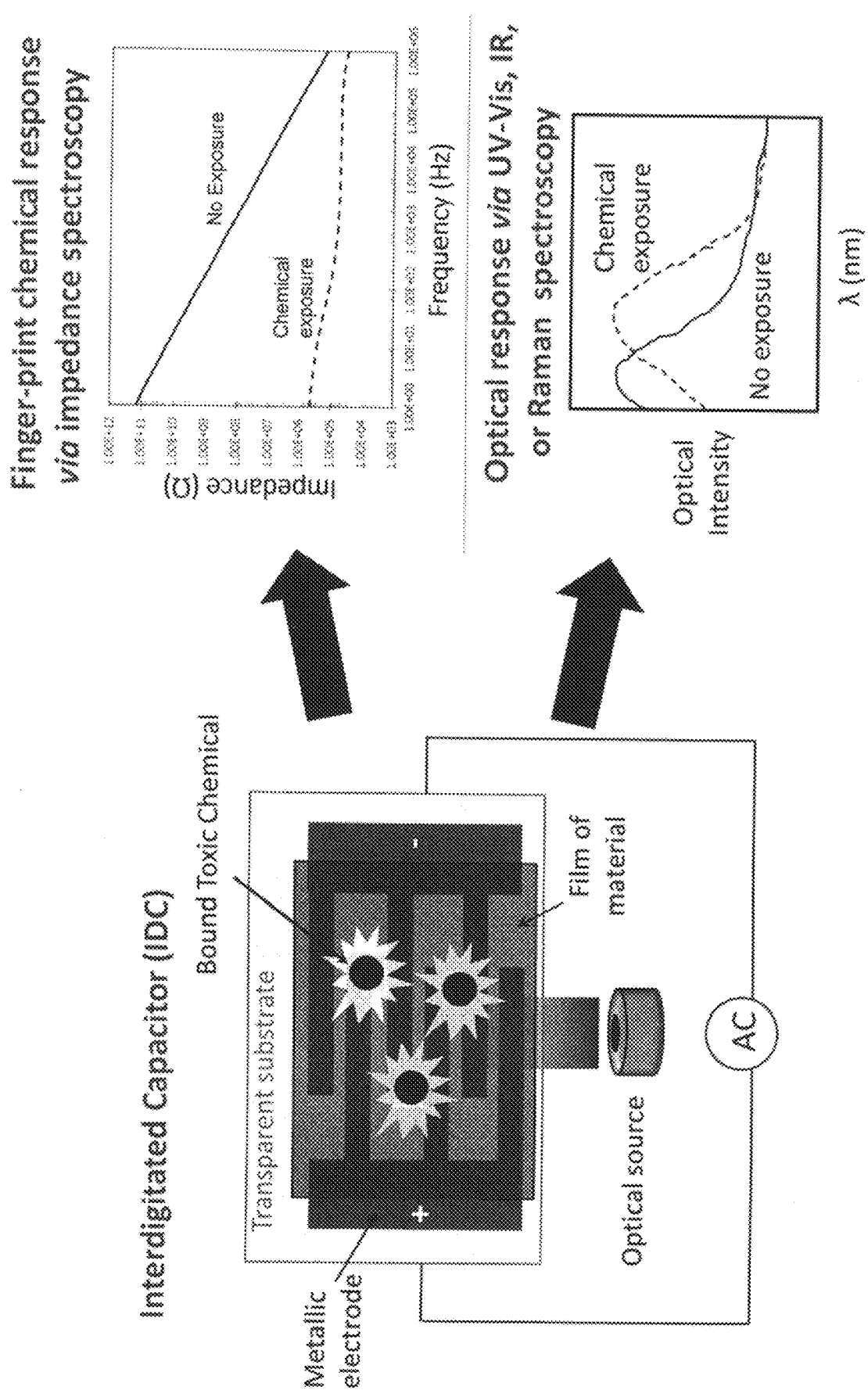
FIG. 11 shows a schematic drawing of the self-indicating colorimetric response material fabricated as a film across the surface of an interdigitated capacitor supported on a transparent substrate. As the toxic chemical analyte binds to the film of the material, changes in the optical properties as well as the electrical properties occur. This can be detected by AC impedance and UV-Visible Spectroscopy. The impedance drops significantly by 1 to 5 orders of magnitude depending on the frequency regime from chemical exposure to 2-CEES. In addition, a shift in the visible spectra occurs as the analyte binds to the self-indicating colorimetric response material, leading to an optical response.

The results of Orange self-indicating colorimetric (SIC) v1 response material and cobalt aluminum silicate material (OBZ21R) are depicted in FIG. 7. Significant changes in the UV-Vis spectra were observed for sarin exposure. In summary, this toxic chemical was detectable by changes in the spectrum as measured by UV-Vis.

Results of pre- and post-exposed copper aluminum silicate material (UBZ31R) are depicted in FIG. 8. Significant changes in the UV-Vis spectra were observed for sulfur mustard. In summary, this toxic chemical was detectable by changes in the spectrum as measured by UV-Vis.

Results of cobalt aluminum silicate material (OBZ21R) are depicted in FIG. 9. Significant changes in the UV-Vis spectra were observed for sarin. In summary, this toxic chemical was detectable by changes in the spectrum as measured by UV-Vis.

To summarize these results collected from the UV-Vis spectra shown in FIG. 6-9, FIG. 10 depicts the mapping of the colorimetric response of these materials to the analyte using a L*, a*, and b* color space axes plot.

Example 38: Detection of the Presence of Toxic Chemicals by Spectroscopy

The M-aluminum silicates of Example D, the M-aluminum titanium silicates of Example E, and the M-aluminum titanium phosphorus silicates of Example F, each in film form, are used for the detection of the toxic chemicals, e.g. G-type, V-type, and H-type chemical agents as well as opioids. The spectral status is detected by AC impedance spectroscopy. Briefly, data were collected on pre- and post-exposed interdigitated capacitors (IDCs) coated with the sorbent materials as films on the surface of a transparent alumina substrate to a toxic chemical. One of the instruments used to collect the data was a Solartron Analytical 1260 impedance analyzer equipped with a 1296 dielectric interface. AC impedance measurements were collected over a frequency range of $10^{-2}$ to $10^{6}$ Hz with an applied voltage of 100 mV, and the dwell time was 1 s with 5 points measured per frequency decade. Measurements were repeated 3 times and then averaged. The other instrument used to collect the data was a JASCO V-750 spectrophotometer. Scans were collected from 200 to 800 nm, and the background was subtracted. These results are shown in FIG. 11.

The results of nickel aluminum silicate material (IBZ31R) are depicted in FIG. 11. Significant changes in both the impedance and UV-Vis spectra were observed for dimethyl chlorophosphate (DMCP), which is noted as chemical exposure in FIG. 11. In summary, this toxic chemical was detectable by changes in the spectrum as measured by impedance and UV-Vis; thus this IDC has multifunctional detection and/or sensing of toxic chemicals.

REFERENCES

1 Peterson, G. W., Karwacki, C. J., Feaver, W. B. & Rossin, J. A. Zirconium Hydroxide as a Reactive Substrate for the Removal of Sulfur Dioxide. *Industrial & Engineering Chemistry Research* 48, 1694-1698, doi: 10.1021/ie801403h (2009).

2 Peterson, G. W., Wagner, G. W., Keller, J. H. & Rossin, J. A. Enhanced Cyanogen Chloride Removal by the Reactive Zirconium Hydroxide Substrate. *Industrial & Engineering Chemistry Research* 49, 11182-11187, doi: 10.1021/ie101204e (2010).

3 Peterson, G. W., Rossin, J. A., Karwacki, C. J. & Glover, T. G. Surface Chemistry and Morphology of Zirconia Polymorphs and the Influence on Sulfur Dioxide Removal. *Journal of Physical Chemistry C* 115, 9644-9650, doi: 10.1021/jp201173x (2011).

4 Peterson, G. W. & Rossin, J. A. Removal of Chlorine Gases from Streams of Air Using Reactive Zirconium Hydroxide Based Filtration Media. *Industrial & Engineering Chemistry Research* 51, 2675-2681, doi: 10.1021/ie200809r (2012).

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A chemical sensor, comprising:

a sorbent comprising a porous metal oxide/hydroxide or a porous mixed-metal oxide/hydroxide, said porous metal oxide/hydroxide or porous mixed-metal oxide/hydroxide including a transition metal containing reactant configured to react with one or more toxic chemicals or byproducts thereof, wherein said sorbent is applied as a film across a surface of a substrate, and wherein changes in optical properties and electrical properties occur as a toxic chemical binds to the film and said changes are used to detect a presence of the toxic chemical.

2. The sensor of claim 1, wherein said porous metal oxide/hydroxide or porous mixed-metal oxide/hydroxide is selected from the group consisting of: silicon-aluminum oxide/hydroxide; silicon-aluminum-titanium oxide/hydroxide, silicon-aluminum-titanium-phosphorus oxide/hydroxide; zirconium oxide/hydroxide; vanadium oxide/hydroxide; iron oxide/hydroxide; manganese oxide/hydroxide; cobalt oxide/hydroxide; copper oxide/hydroxide; nickel oxide/hydroxide; niobium oxide/hydroxide; tantalum oxide/hydroxide; molybdenum oxide/hydroxide; tungsten oxide/hydroxide; chromium oxide/hydroxide; or mixtures thereof.

3. The sensor of claim 2, wherein said silicon-aluminum oxide/hydroxide has a silicon to aluminum ratio of from 3 to 1,000, said silicon-aluminum-titanium oxide/hydroxide has a silicon to aluminum ratio of from 3 to 1000 and a silicon to titanium ratio of 2 to 500, and said silicon-aluminum-titanium-phosphorus oxide/hydroxide has a silicon to aluminum ratio of from 3 to 1,000, a silicon to titanium ratio of 2 to 500, and a titanium to phosphorus ratio of 1 to 500.

4. The sensor of claim 3, wherein said silicon-aluminum oxide/hydroxide has a silicon to aluminum ratio of 30, said silicon-aluminum-titanium oxide/hydroxide has a silicon to aluminum ratio of 30 and a silicon to titanium ratio of 2, and said silicon-aluminum-titanium-phosphorus oxide/hydroxide has a silicon to aluminum ratio of 30, a silicon to titanium ratio of 2, and a titanium to phosphorus ratio of 15.

5. The sensor of claim 1, wherein said transition metal containing reactant comprises salts, nitrates, sulfides, chlorides, oxides, or oxyhydroxides of cobalt, copper, iron, manganese, nickel, chromium, lanthanides, or mixtures thereof.

6. The sensor of claim 1, wherein said sorbent is fabricated, deposited, or spray-coated on the substrate and said substrate is selected from the group consisting of: fabrics, stainless steel, glass, wood, cement, ceramic, graphite, asphalt, land or aerial vehicle bodies, fiber optic cables, insulating substrates, semi-conducting substrates, and conducting substrates.

7. The sensor of claim 1, wherein a plurality of said sorbents are disposed in an array for detection or sensing of the toxic chemicals.

* * * * *